(12) United States Patent
Dodo

(10) Patent No.: US 7,998,183 B2
(45) Date of Patent: Aug. 16, 2011

(54) HEAT GENERATING BODY

(75) Inventor: Toshihiro Dodo, Kanagawa (JP)

(73) Assignee: Mycoal Co., Ltd., Tochigi-Shi (JP)

( * ) Notice: Subject to any disclaimer, the term of this patent is extended or adjusted under 35 U.S.C. 154(b) by 909 days.

(21) Appl. No.: 11/632,122

(22) PCT Filed: Jul. 14, 2005

(86) PCT No.: PCT/JP2005/013015
§ 371 (c)(1),
(2), (4) Date: Dec. 12, 2007

(87) PCT Pub. No.: WO2006/006662
PCT Pub. Date: Jan. 19, 2006

(65) Prior Publication Data
US 2008/0200971 A1    Aug. 21, 2008

(30) Foreign Application Priority Data
Jul. 14, 2004    (JP) ................................ 2004-207843

(51) Int. Cl.
*A61F 7/00* (2006.01)
*A61F 7/02* (2006.01)
*A61F 7/08* (2006.01)

(52) U.S. Cl. ............ 607/114; 607/96; 607/108; 607/112

(58) Field of Classification Search .................. 607/108, 607/114
See application file for complete search history.

(56) References Cited

U.S. PATENT DOCUMENTS

| | | | | |
|---|---|---|---|---|
| 3,900,035 A | * | 8/1975 | Welch et al. .................. | 607/108 |
| 5,046,479 A | | 9/1991 | Usui | |
| 5,084,986 A | | 2/1992 | Usui | |
| 5,674,270 A | * | 10/1997 | Viltro et al. .................... | 607/112 |
| 5,741,318 A | * | 4/1998 | Ouellette et al. .............. | 607/108 |
| 5,837,005 A | * | 11/1998 | Viltro et al. .................... | 607/112 |

(Continued)

FOREIGN PATENT DOCUMENTS

JP    11-253477    9/1999

(Continued)

OTHER PUBLICATIONS

U.S. Appl. No. 10/450,441, filed May 4, 2004, Usui et al.

(Continued)

*Primary Examiner* — Roy D Gibson
*Assistant Examiner* — Kaitlyn E Helling
(74) *Attorney, Agent, or Firm* — Kratz, Quintos & Hanson, LLP

(57) ABSTRACT

A heat generating body wherein three or more plural sectional exothermic parts are provided at intervals via a sectioned part which is a heat seal part. The sectional exothermic parts have a heat generating composition capable of causing heat generation upon contact with oxygen in air and are at least constituted of three kinds of a low temperature sectional exothermic part, a middle temperature sectional exothermic part and a high temperature sectional exothermic part. A maximum temperature of the high temperature sectional exothermic part is higher than a maximum temperature of the low temperature sectional exothermic part. A maximum temperature of the middle temperature sectional exothermic part is between a maximum temperature of the high temperature sectional exothermic part and a maximum temperature of the low temperature sectional exothermic part. The middle temperature sectional exothermic part is constituted of plural sectional exothermic parts having a different maximum temperature.

6 Claims, 5 Drawing Sheets

U.S. PATENT DOCUMENTS

| | | | | |
|---|---|---|---|---|
| 5,860,945 A | * | 1/1999 | Cramer et al. | 602/62 |
| 5,984,953 A | * | 11/1999 | Sabin et al. | 607/114 |
| 2006/0154006 A1 | | 7/2006 | Usui et al. | |
| 2008/0029079 A1 | * | 2/2008 | Dodo | 126/263.01 |

FOREIGN PATENT DOCUMENTS

| | | |
|---|---|---|
| JP | 2000-296145 | 10/2000 |
| JP | 2000-300592 | 10/2000 |
| JP | 2001-230 | 1/2001 |
| JP | 2002-155273 | 5/2002 |
| JP | 2003-509120 | 3/2003 |
| JP | 2003-204983 | 7/2003 |
| JP | 2003-220087 | 8/2003 |
| JP | 2003-336042 | 11/2003 |

OTHER PUBLICATIONS

U.S. Appl. No. 10/450,521, filed Jun. 19, 2003, Usui et al.
U.S. Appl. No. 10/451,634, filed Jul. 9, 2003, Usui et al.
U.S. Appl. No. 10/386,723, filed Mar. 13, 2003, Usui.
U.S. Appl. No. 10/475,513, filed Oct. 27, 2003, Usui et al.
U.S. Appl. No. 10/524,211, filed Feb. 10, 2005, Usui et al.

\* cited by examiner

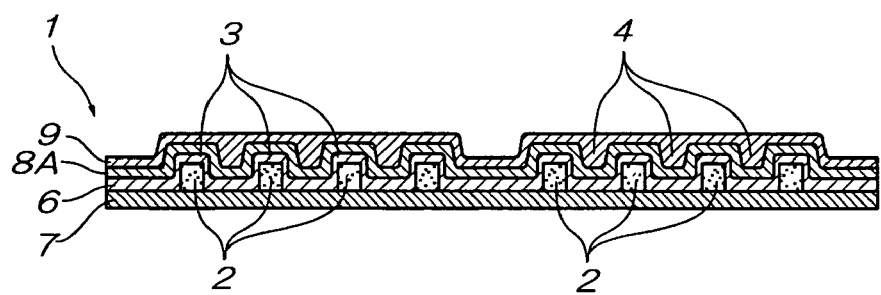
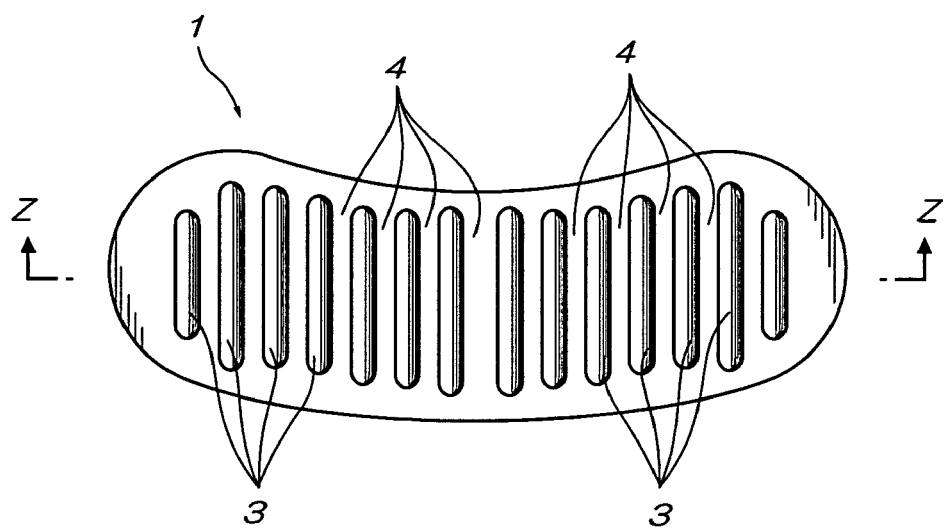
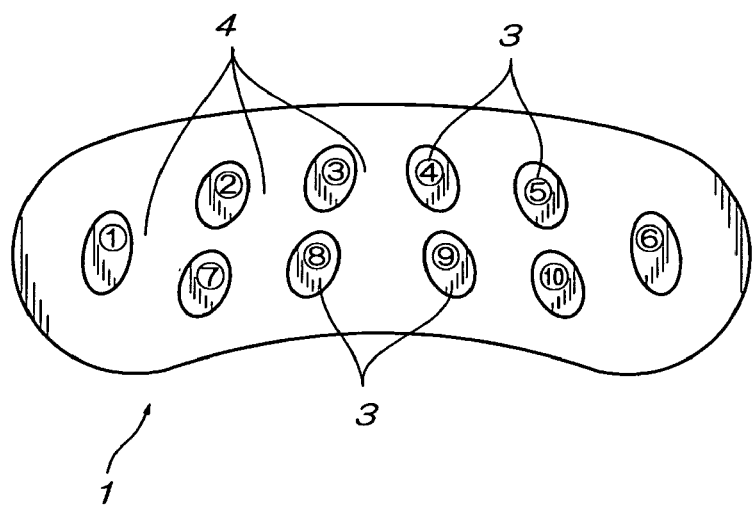

FIG. 7(a)    FIG. 7(b)    FIG. 7(c)
 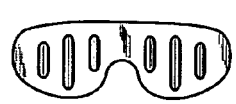 
FIG. 7(d)    FIG. 7(e)    FIG. 7(f)
 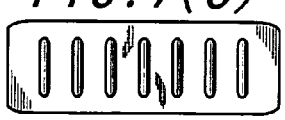 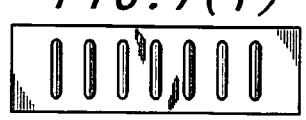
FIG. 7(g)    FIG. 7(h)    FIG. 7(i)
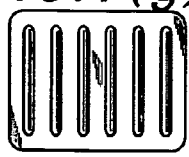 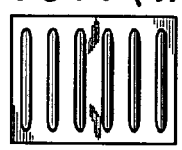 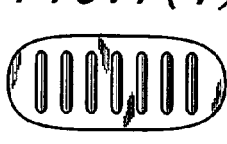
FIG. 7(j)    FIG. 7(k)    FIG. 7(l)
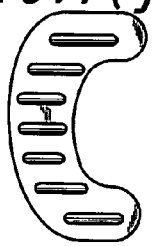 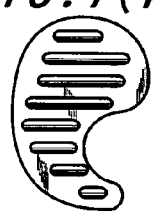 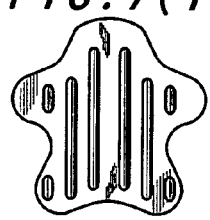
FIG. 7(m)    FIG. 7(n)    FIG. 7(o)
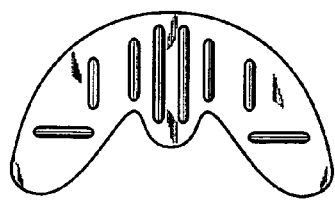 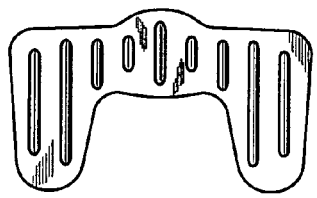 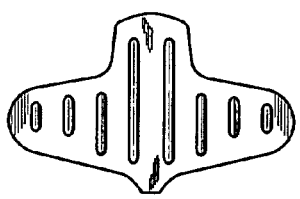
FIG. 7(p)    FIG. 7(q)
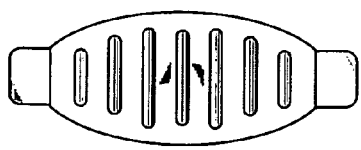 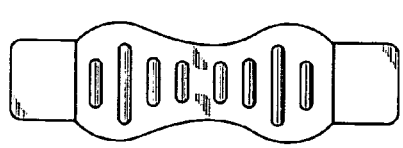

HEAT GENERATING BODY

This application is being cross referenced with the following fifteen applications filed on even date herewith:

| Inventors | Title | Int'l Appln No. |
|---|---|---|
| DODO, Toshihiro | PROCESS FOR PRODUCING HEAT GENERATING MIXTURE, HEAT GENERATING MIXTURE, HEAT GENERATING COMPOSITION, AND HEAT GENERATING BODY | PCT/JP05/012998 |
| DODO, Toshihiro | ACTIVE IRON POWDER, HEAT GENERATING COMPOSITION, AND HEAT GENERATING | PCT/JP05/012999 |
| DODO, Toshihiro | ACTIVE IRON POWDER AND HEAT GENERATING BODY | PCT/JP05/013000 |
| DODO, Toshihiro | HEAT GENERATING COMPOSITION, HEAT GENERATING BODY, AND PROCESS FOR PRODUCING HEAT GENERATING BODY | PCT/JP05/013001 |
| DODO, Toshihiro | WETTABLE HEAT GENERATING COMPOSITION COMPRESSED BODY, HEAT GENERATING BODY, AND PROCESS FOR PRODUCING WETTABLE HEAT GENERATING COMPOSITION COMPRESSED BODY | PCT/JP05/013002 |
| DODO, Toshihiro | HEAT GENERATING BODY AND PROCESS FOR PRODUCING HEAT GENERATING BODY | PCT/JP05/013003 |
| DODO, Toshihiro | HEAT GENERATING BODY AND PROCESS FOR PRODUCING THE SAME | PCT/JP05/013004 |
| DODO, Toshihiro | HEAT GENERATING BODY | PCT/JP05/013005 |
| DODO, Toshihiro | MICROHEATER AND PROCESS FOR PRODUCING THE SAME | PCT/JP05/013006 |
| DODO, Toshihiro | HEAT CLOTH AND PROCESS FOR PRODUCING THE SAME | PCT/JP05/013007 |
| DODO, Toshihiro | HEAT GENERATING PAD AND METHOD OF USE OF THE SAME | PCT/JP05/013008 |
| DODO, Toshihiro | HEAT GENERATING BODY | PCT/JP05/013009 |
| DODO, Toshihiro, et al. | FOOT WARMING HEAT GENERATING BODY AND PROCESS FOR PRODUCING FOOT WARMING HEAT GENERATING BODY | PCT/JP05/013011 |
| DODO, Toshihiro | HEAT GENERATING BODY, HEAT INSULATING METHOD USING THE SAME AND PACKAGING MATERIAL FOR DIE MOLDING HEAT GENERATION | PCT/JP05/013014 |
| DODO, Toshihiro | FLEXIBLE HEAT GENERATING BODY | PCT/JP05/013017 |

TECHNICAL FIELD

The present invention relates to a heat generating body which even when used over a long period of time, hardly imparts an unwell feeling due to a high temperature, is fit to curved surface parts such as the abdominal region and the waist and is able to achieve effective warming.

BACKGROUND ART

As a heat generating body, various heat generating bodies which are fixed to clothes or the skin and used for warming the abdominal region, the waist and so on have been proposed.

There have been proposed heat generating bodies in which two kinds of temperature bands of a high temperature part and a low temperature part are provided and heat generating bodies in which a high temperature part is subjected to heat generation within a short period of time to enhance rising properties and the temperature is kept in a low temperature part over a long period of time.

However, in conventional heat generating bodies, since a portion with which a heat generating body is brought into contact is warmed entirely and similarly, there was involved such a problem that when the heat generating body is put on a user over a long period of time, the user feels excessively high so that continuation of the use becomes difficult or an unwell feeling is generated. For that reason, though it may be thought that the temperature of a heat generating body is made entirely low, effects by a thermal stimulus such as an effect for relaxation of menstrual pain cannot be expected thereby. Also, such a heat generating body was not fit along curved surfaces such as the abdominal region and the waist and was problematic in a feeling for use.

Also, in the case where a high temperature part is partially provided in a low temperature part, when a maximum temperature of the high temperature part is raised and exothermic rising properties are improved, there was a fear that the temperature increases too much, thereby producing a burn. Also, when an exothermic part is constituted of two kinds of a high temperature part and a low-temperature part, a warming effect by a temperature stimulus was insufficient because a large temperature difference between the high temperature part and the low temperature cannot be taken. Also, when the width of the exothermic part is large, it was difficult to reveal this effect because flexibility is lost. Also, though the heat generating body is bent in a connecting part, a feeling for use was worse because a rough and hardened feeling remains.

Also, there is seen a tendency that body warmers are changed from a small size to a large size, thereby warming a wide range. However, when a large-sized body warmer is constituted of a gathering of plural sectional exothermic parts, though the warmth could be taken, heat retained too much in the center, thereby possibly causing a burn. There has been demanded a heat generating body which is able to warm a wide range safely and comfortably over a long period of time.

Also, when a peak temperature is raised to improve exothermic rising properties, the temperature control is difficult. When a high temperature is provided for the purpose of obtaining a sufficient feeling for effect immediately after the use, the temperature becomes too high for a while, thereby causing excessive heating.

DISCLOSURE OF THE INVENTION

Problems that the Invention is to Solve

Accordingly, an object of the invention is to provide a heat generating body which nevertheless an excellent warming effect (for example, an effect for relaxation of a pain by a thermal stimulus) can be obtained, hardly provides a user with an unwell feeling due to a high temperature, is fit to curved surface parts such as the abdominal region and the waist and is able to comfortably warm a desired site with a good feeling for use over a long period of time.

Means for Solving the Problems

As set forth in claim 1, a heat generating body of the invention is a heat generating body wherein three or more plural sectional exothermic parts are provided at intervals via a sectioned part which is a heat seal part, which is characterized in that:

the sectional exothermic parts have a heat generating composition capable of causing heat generation upon contact with oxygen in air and are at least constituted of three kinds of a low temperature sectional exothermic part, a middle temperature sectional exothermic part and a high temperature sectional exothermic part;

a maximum temperature of the high temperature sectional exothermic part is higher than a maximum temperature of the low temperature sectional exothermic part;

a maximum temperature of the middle temperature sectional exothermic part is laid between a maximum temperature of the high temperature sectional exothermic part and a maximum temperature of the low temperature sectional exothermic part; and the middle temperature sectional exothermic part is constituted of plural sectional exothermic parts having a different maximum temperature.

Also, a heat generating body as set forth in claim 2 is characterized in that in the heat generating body as set forth in claim 1, the heat generating composition is a moldable heat generating composition which contains, as essential components, an iron powder, a carbon component, a reaction accelerator and water, does not contain a flocculant aid, a flocculant, an agglomeration aid, a dry binder, a dry binding agent, a dry binding material, a sticky raw material, a thickener and an excipient, contains surplus water so as to have a water mobility value of from 0.01 to 20, has moldability due to the surplus water which is a connecting substance, with the water in the heat generating composition not functioning as a barrier layer, and is capable of causing an exothermic reaction upon contact with air;

a heat generating composition molded body as formed by molding the moldable heat generating composition is laminated on a substrate, a covering material is put thereon, and the periphery of the heat generating composition molded body is heat sealed to form the sectional exothermic parts;

the substrate is substantially planar and does not have a pocket, an accommodating division or an accommodating zone;

the heat generating composition molded body has a volume of from 0.1 to 30 cm$^3$;

a ratio of the capacity of the sectional exothermic parts to the volume of the heat generating composition molded body is from 0.6 to 1.0;

the sectioned exothermic parts have a maximum height of from 0.1 to 10 mm;

the sectioned part between the sectional exothermic parts has a width of from 0.3 to 50 mm; and the substrate or the covering material has permeability to air.

Also, a heat generating body as set forth in claim 3 is characterized in that in the heat generating body as set forth in claim 1, the low temperature sectional exothermic part, the middle temperature sectional exothermic part and the high temperature sectional exothermic part are determined by a center distance method.

Also, a heat generating body as set forth in claim 4 is characterized in that in the heat generating body as set forth in claim 1, the heat generating body has the low temperature sectional exothermic part in each end part thereof.

Also, a heat generating body as set forth in claim 5 is characterized in that in the heat generating body as set forth in claim 1, on the surface orthogonal to the thickness of the heat generating body, a bending resistance in at least one direction is not more than 100 mm.

Also, a heat generating body as set forth in claim 6 is characterized in that in the heat generating body as set forth in claim 1, the heat generating body has a fixing measure on at least a part of the exposed surface thereof.

Also, the heat generating body is characterized in that the amount of air of the high temperature sectional exothermic part is larger than those of the low temperature sectional exothermic part and the middle sectional exothermic part.

Also, the heat generating body is characterized in that the planar area of the high temperature sectional exothermic part is larger than those of the low temperature sectional exothermic part and the middle temperature sectional exothermic part.

Also, the heat generating body is characterized in that the fixing measure is an adhesive layer; and that the adhesive layer contains at least one member selected from additional components consisting of a water retaining agent, a water absorptive polymer, a pH adjusting agent, a surfactant, an organosilicon compound, a hydrophobic polymer compound, a pyroelectric substance, an antioxidant, an aggregate, a fibrous substance, a moisturizer, a functional substance, and a mixture thereof.

Advantages of the Invention

According to the foregoing constitutions, it has become possible to provide a heat generating body which is able to be used warmly and comfortably immediately after the use, is able to obtain an excellent warming effect during the use and has well fitness and an excellent feeling for use by:

1) making exothermic rising fast without increasing a maximum temperature, namely making it warm with the start of use, and not providing warmth too much, 2) making the temperature band such that it is constituted of three or more kinds, thereby mildly changing a large temperature difference, 3) making the width of the temperature band small, thereby making the temperature band fine or thin, and 4) combining them.

BEST MODES FOR CARRYING OUT THE INVENTION

As described previously, according to the invention, by constituting a heat generating body by plural sectional exothermic parts and changing a maximum temperature among the respective sectional exothermic parts, it has become possible to complete a heat generating body which is large in size and is able to take safe and comfortable warmth in a wide range over a long period of time.

In the invention, by providing three or more kinds of temperature ranges, it has become possible to set up an inclined temperature, thereby making it possible to give a thermal stimulus and to achieve warming over a long period of time.

Furthermore, there are obtained various types of temperature distribution due to, for example, a gradual change in the temperature, a random change in the temperature, and the production of a stimulating temperature.

In the invention, the temperature distribution of the heat generating body can be determined by a center distance method.

The "center distance method" as referred to herein is to determine the temperature distribution of the heat generating body by relatively expressing a temperature difference between a center point of one sectional exothermic part and a center point of each of the surrounding sectional exothermic parts.

In detail, it can be determined by the following method.

First of all, it is assumed that sectional exothermic parts in the number of n in total are present in one heat generating body (i=1 to $\overline{n}$); and that each of the sectional exothermic parts has a load factor (Fi). Incidentally, though the load factor (Fi) is not limited, it is preferably an exothermic ability (for example, composition and compression rate), an amount of air, or an area of the heat generating composition.

Next, one sectional exothermic part is fixed, and a distance (Li) from the center point of this sectional exothermic part to each of the remaining sectional exothermic parts is determined. Then, a load which each of the remaining sectional exothermic parts exerts on the one sectional exothermic part is defined as (Fi/Li), and the total sum of the load which each of the remaining sectional exothermic parts exerts on the one sectional exothermic part is determined according to the following expression, thereby defining a total sum value (T) as a temperature factor.

$$T=(F1+F2+\ldots Fn-1/L1+L2+\ldots Ln-1)$$

The temperature factor (T) is determined with respect to all the sectional exothermic parts (T1 to Tn). A sectional exothermic part where this temperature factor is the maximum is a maximum sectional exothermic part, whereas a sectional exothermic part where the temperature factor is the minimum is a minimum sectional exothermic part.

In this way, the high temperature exothermic part, the middle temperature exothermic part and the low temperature exothermic part can be determined.

Incidentally, the load factor (Fi) can be expressed as follows.

$$Fi=\text{(Ability factor)}+\text{(Air factor)}+\text{(Area factor)}+\text{(Height factor)}$$

Ability factor: (Exothermic ability of heat generating composition in sectional exothermic part)/(Maximum exothermic ability of heat generating composition in sectional exothermic part in heat generating body)

Air factor: (Amount of air of sectional exothermic part)/(Maximum amount of air of sectional exothermic part in heat generating body)

Area factor: (Area of sectional exothermic part)/(Maximum area of sectional exothermic part in heat generating body)

Height factor: (Height of sectional exothermic part)/(Maximum height of sectional exothermic part in heat generating body)

Incidentally, in the case where the respective factors of all the sectional exothermic parts are identical, the ability factor, the air factor, the area factor and the height factor are all 1. Furthermore, the area factor or the height factor may be defined as an area or a height of the heat generating composition in the sectional exothermic part.

That is, the temperature distribution to be determined by the center distance method is determined while making a heat insulating effect of a certain sectional exothermic part as obtained from the surrounding sectional exothermic parts as the major factor. For example, in the case where the respective sectional exothermic parts are identical with respect to the exothermic ability, the amount of air, the area and the height, the larger the number of the sectional exothermic parts existing within a short distance, the higher the heat insulating effect and the higher the maximum exothermic temperature. Furthermore, in the case where the sectional exothermic parts existing within a short distance are identical, the larger the number of the sectional exothermic parts existing within a next long distance, the higher the heat insulating effect. The same can be said consecutively.

Putting all accounts together, the overall heat insulating effect of the surrounding sectional exothermic parts to the center point of each sectional exothermic part becomes clear so that the relative temperature distribution is estimated.

By combining this with, as the ability factor, component species, composition, compression rate, thickness or volume of the heat generating composition, air permeability of the air-permeable part, area, height or volume of the sectional exothermic part, or the like, it is possible to section the high temperature sectional exothermic part, the middle temperature sectional exothermic part and the low temperature sectional exothermic part, respectively. Accordingly, by subdividing the high temperature sectional exothermic part, the middle temperature sectional exothermic part and the low temperature sectional exothermic part, respectively on the basis of the center distance method, it is possible to prepare a heat generating body having a variety of temperature distribution in which the disposition of the sectional exothermic parts are changed.

In the invention, it should be construed that the heat generating composition molded body includes a heat generating composition compressed body, too.

In the sectional exothermic part or the heat generating composition molded body of the invention, its maximum width is usually from 0.5 to 60 mm, preferably from 0.5 to 50 mm, more preferably from 1 to 50 mm, further preferably from 3 to 50 mm, still further preferably 3 to 30 mm, even further preferably from 5 to 20 mm, even still further preferably from 5 to 15 mm, and most preferably from 5 to 10 mm. Furthermore, its maximum height is usually from 0.1 to 30 mm, preferably from 0.1 to 10 mm, more preferably from 0.3 to 10 mm, further preferably from 1 to 10 mm, and still further preferably from 2 to 10 mm. Moreover, its longest length is usually from 5 to 300 mm, preferably from 5 to 200 mm, more preferably from 5 to 100 mm, further preferably from 20 to 150 mm, and still further preferably from 30 to 100 mm.

A capacity of the sectional exothermic part or a volume of the heat generating composition molded body is usually from 0.015 to 500 $cm^3$, preferably from 0.04 to 30 $cm^3$, more preferably from 0.1 to 30 $cm^3$, further preferably from 1 to 30 $cm^3$, and still further preferably from 3 to 20 $cm^3$.

In the sectional exothermic part, when the sectional exothermic part which is an accommodating region of the heat generating composition is filled with the heat generating composition molded body, a volume ratio of the volume of the heat generating composition molded body which is an occupying region of the heat generating composition molded body to the capacity of the sectional exothermic part which is an accommodating region of the heat generating composition is usually from 0.6 to 1, preferably from 0.7 to 1, more preferably from 0.8 to 1, and further preferably from 0.9 to 1.0.

Furthermore, a width of the sectioned part which is a space between the sectional exothermic parts is not limited so far as sectioning can be achieved. It is usually from 0.1 to 50 mm, preferably from 0.3 to 50 mm, more preferably from 0.3 to 50 mm, further preferably from 0.3 to 40 mm, still further preferably from 0.5 to 30 mm, even further preferably from 1.0 to 20 mm, and even still further preferably from 3 to 10 mm.

Incidentally, the heat generating composition molded body or the sectional exothermic part may have any shape. The shape may be a planar shape, and examples thereof include a circular shape, an elliptical shape, a polygonal shape, a star shape, and a flower shape. Also, the shape may be a three-dimensional shape, and examples thereof include a polygonal pyramidal shape, a conical shape, a frustum shape, a spherical shape, a parallelepiped shape, a cylindrical shape, a semi-pillar shape, a semicylindroid shape, a semicylidrical shape, a pillar shape, and a cylindroid shape. Furthermore, in these shapes, the corner may be rounded, thereby processing the corner in a curvilinear or curved state, or the central part may be provided with a concave.

Furthermore, the "volume of the heat generating composition molded body of the invention" as referred to herein means a volume of the heat generating composition molded body or compressed heat generating composition molded body.

Furthermore, the "capacity of the sectional exothermic part" as referred to herein means an internal capacity of the sectional exothermic part having a heat generating composition molded body accommodated therein.

Furthermore, the sectionalization can be made in arbitrary directions such as a length or width direction, length and width directions, and an oblique direction. In particular, an exothermic part in which two or more sectional exothermic parts are provided in a striped form is preferable.

The "water mobility value" as referred to herein is a value showing an amount of surplus water which can transfer to the outside of the heat generating composition in water present in the heat generating composition. This water mobility value will be described below with reference to FIGS. 8 to 12.

As shown in FIG. 8, a filter paper 13 of No. 2 (second class of JIS P3801) in which eight lines are drawn radiating from the central point with an interval of 45° is placed on a stainless steel plate 17 as shown in FIGS. 9 and 10; a template 14 having a size of 150 mm in length×100 mm in width and having a hollow cylindrical hole 15 having a size of 20 mm in inner diameter×8 mm in height is placed in the center of the filter paper 13; a sample 16 is placed in the vicinity of the hollow cylindrical hole 15; and a stuffer plate 10 is moved on and along the template 14 and inserted into the hollow cylindrical hole 15 while stuffing the sample 16, thereby leveling the sample (force-in die molding).

Next, as shown in FIG. 11, a non-water absorptive 70 µm-thick polyethylene film 12 is placed so as to cover the hole 15, and a flat plate 11 made of stainless steel having a size of 5 mm in thickness×150 mm in length×150 mm in width is further placed thereon and held for 5 minutes such that an exothermic reaction is not caused.

Thereafter, a shown in FIG. 12, the filter paper 13 is taken out, and an oozed-out locus of the water or aqueous solution is read as a distance 18 (unit: mm) from a periphery 19 as an edge of the hollow cylindrical hole to an oozed-out tip along the radiating lines. Similarly, a distance 18 from each of the lines is read, and eight values in total are obtained. Each of the eight values (a, b, c, d, e, f, g and h) which are read out is defined as a measured water content value. An arithmetic average value of the eight measured water content values is defined as a water content value (mm) of the sample.

Furthermore, the water content for the purpose of measuring a real water content value is defined as a compounded water content of the heat generating composition corresponding to the weight of the heat generating composition having a size of 20 mm in inner diameter×8 mm in height or the like, similar measurement is conducted only with water corresponding to that water content, and a value as calculated in the same manner is defined as a real water content value (mm). A value obtained by dividing the water content value by the real water content value and then multiplying with 100 is a water mobility value.

That is, the water mobility value is represented by the following expression.

$$(\text{Water mobility value}) = \{[\text{Water content value(mm)}]/[(\text{Real water content value(mm)})]\} \times 100$$

With respect to the same sample, five points are measured, and the five water mobility values are averaged, thereby defining an average value thereof as a water mobility value of the sample.

In the invention, the water mobility value (0 to 100) is preferably from 0.01 to 20, more preferably from 0.01 to 18, further preferably from 0.01 to 15, still further preferably from 0.01 to 13, even further preferably from 1 to 13, and even still further preferably from 3 to 13.

A heat generating composition having a water mobility value of less than 0.01 is insufficient in moldability. A heat generating composition having a water mobility value of from 0.01 to 50 has moldability and therefore, is a moldable heat generating composition. When the water mobility value exceeds 20, it is necessary that a part of water of the heat generating composition is removed by water absorption, dehydration, etc. That is, unless a part of water in the heat generating composition molded body is removed by water absorption, dehydration, etc. using a water absorptive packaging material, etc., a practical useful exothermic reaction is not caused. Incidentally, in the case where a water absorptive polymer having a low water absorption speed is used and although a high water mobility value is exhibited at the time of molding, after elapsing a certain period of time, a part of surplus water is taken in the water absorptive polymer, whereby the heat generating composition becomes in an exothermic state with a water mobility value of from 0.01 to 20, even a heat generating composition having a high water mobility value is dealt as a heat generating composition in which surplus water does not function as a barrier layer. In a heat generating composition having a water mobility value exceeding 50, surplus water is too much, the heat generating composition becomes in a slurry state and loses moldability, and the surplus water functions as a barrier layer. Thus, even upon contact with air as it is, an exothermic reaction is not caused.

Furthermore, the "water mobility value" as referred to herein is a value obtained by digitizing surplus water which is the water content capable of being easily and freely oozed out the system in water which is contained in the heat generating composition or mixture or the like. In a mixture in which some components of the heat generating composition or mixture or the like are mixed, the amount of the surplus water is variously changed depending the amount of a component having a water retaining ability such as a water retaining agent, a carbon component and a water absorptive polymer and wettability of each component, and therefore, it is every difficult to predict the water mobility value from the amount of addition of water. Accordingly, since the amount of surplus water of the heat generating composition or mixture of the like is determined from the water mobility value, by determining the amount of addition of water and the amount of other components, a heat generating composition or mixture or the like having a substantially fixed amount of surplus water is obtained with good reproducibility. That is, by previously examining the water mobility value and a composition ratio of a heat generating composition or mixture or the like, a heat generating composition or mixture or the like as compounded along that composition ratio has a water mobility value falling within a fixed range, namely, an amount of surplus water falling within a fixed range. Thus, it is possible to easily produce a variety of heat generating compositions such as a powdered heat generating composition which causes heat generation upon contact with air but does not have moldability, a heat generating composition which causes heat generation upon contact with air and has moldability, and a heat generating composition which, after discharging out a fixed amount of surplus water from the system by water absorption, etc., causes heat generation upon contact with air and has moldability. Accordingly, if the water mobility value is known, it is possible to note what state does the subject heat generating composition or mixture or the like take.

If the water mobility value is employed, it is possible to embody a desired state with good reproducibility by a simple measurement. Thus, it becomes possible to determine a component ratio of the heat generating composition on the basis of the water mobility value obtained by the measurement and the component ratio, thereby simply achieving actual production of a heat generating composition.

As a use example of the water mobility value, water (or a reaction accelerator aqueous solution) is added to and mixed with a mixture of specified amounts of heat generating composition components exclusive of water (or a reaction accelerator aqueous solution), thereby producing plural heat generating compositions having a different water content. Next, a water mobility value of each of the heat generating compositions is measured, thereby determining a relationship between the amount of addition of water (or a reaction accelerator aqueous solution) and a water mobility value.

A heat generating composition which has moldability and causes heat generation upon contact with air has a water mobility value of from 0.01 to 20. By determining a compounding ratio of the respective components therefrom to prepare a mixture in this compound ratio, a moldable heat generating composition in which water does not function as a barrier layer and which has moldability causes heat generation upon contact with air can be produced with good reproducibility.

In this way, since surplus water is used as a connecting substance and a flocculant aid or a dry binding material is not used, reaction efficiency of the iron powder does not drop. Thus, an exothermic performance can be obtained in a small amount as compared with the case of using a flocculant aid or a dry binding material.

Incidentally, in the invention, what water does not function as a barrier layer and causes an exothermic reaction upon contact with air means that water in a heat generating composition does not function as a barrier layer which is an air intercepting layer and immediately after the production of a heat generating composition, comes into contact with air, thereby immediately causing an exothermic reaction.

By using a moldable heat generating composition containing this surplus water as a connecting substance, it becomes possible to produce, for example, a super thin and super flexible heat generating body having plural sectional exothermic parts of a heat generating composition molded body on a substantially planar substrate in a maximum width of preferably from 1 to 50 mm, and more preferably from 1 to 20 mm, or in a maximum diameter of preferably from 1 to 50 mm, and more preferably from 1 to 20 mm (in the case where two or more axes are present as in an ellipse, the major axis is dealt as a length, while the minor axis is dealt as a width).

The "surplus water" as referred to herein means water or an aqueous solution portion which is present excessively in the heat generating composition and easily transfers to the outside of the heat generating composition. The surplus water is defined as a water mobility value which is a value of water or a value of an aqueous solution portion sucked out from the heat generating composition, etc. by a filter paper. When the heat generating composition has an appropriate amount of surplus water, it is assumed that the surplus water causes hydration against hydrophilic groups in the components of the heat generating composition due to a bipolar mutual action or hydrogen bond, etc. and that it is present even in the surroundings of hydrophobic groups while having high structural properties.

This is connecting water as a connecting substance in some meaning. Besides, there is water in a state called as free water which can freely move. When the surplus water increases, the structure is softened, and the free water is found.

The "moldability" as referred to in the invention exhibits that a molded body of the heat generating composition having a cavity or concave die shape is formed by force-through molding using a trimming die having a cavity or cast molding using a concave die, whereby after molding including mold release, the molding shape of the heat generating composition molded body is held.

When the moldability is revealed, since the shape is held until the heat generating composition molded article is at least covered by a covering material and a seal part is formed between the substrate and the covering material, sealing can be achieved in the periphery of the shape with a desired shape. Also, since so-called "spots" which are a collapsed piece of the heat generating composition are not scattered in the seal part, the sealing can be achieved without causing cutting in seal. The presence of the spots causes insufficient sealing.

1) Measurement Device:

With respect to the measurement device, a stainless steel-made molding die (a plate having a size of 2 mm in thickness× 200 mm in length×200 mm in width and having a cavity as treated by R5 in four corners of 60 mm in length×40 mm in width in a central part thereof) and a fixable leveling plate are disposed above a travelable endless belt, and magnets (two magnets having a size of 12.5 mm in thickness×24 mm in length×24 mm in width are disposed in parallel) are disposed under the endless belt.

The magnets should cover a region of the leveling plate and the vicinity thereof and a region larger than a region covered by a cut side (40 mm) vertical to the advancing direction of the cavity of the molding die.

2) Measurement Method:

With respect to the measurement method, a stainless steel plate having a size of 1 mm in thickness×200 mm in length× 200 mm in width is placed on the endless belt of the measurement device, a polyethylene film having a size of 70 μm in thickness×200 mm in length×200 mm in width is placed thereon, and a stainless steel-made molding die is further placed thereon.

Thereafter, a leveling plate is fixed in a position of the cavity of the molding die of 50 mm far from the end portion in the advancing direction of the endless belt, 50 g of a heat generating composition is then placed in the vicinity of the leveling plate between the leveling plate and the cavity, and the heat generating composition is filled in the cavity of the molding die while leveling it by moving the endless belt at 1.8 m/min. After the molding die has completely passed through the leveling plate, the traveling of the endless belt is stopped.

Next, the molding die is removed, and a heat generating composition molded body as laminated on the polyethylene film is observed.

3) Judgment Method:

With respect to the judgment method, in the surroundings of the heat generating composition molded body, in the case where any collapsed piece of the heat generating composition molded body exceeding a maximum length of 800 μm is not present and the number of collapsed pieces of the heat generating composition molded body having a maximum length of from 300 to 800 μm is not more than 5, it is to be noted that the heat generating composition has moldability.

The moldability is an essential property for a heat generating composition to be used in the molding system. If the heat generating composition does not have moldability, it is impossible to produce a heat generating body by the molding system.

The "maximum temperature" as referred to herein is a value as obtained by the measurement under a condition of 30° C. on the surface of a thermal part according to the test (measurement) method of throwaway body warmers as defined in JIS S4100, 1996. A difference between the maximum temperature as generated by the low temperature exothermic part and the maximum temperature as generated by the high temperature exothermic part can be judged by comparing the maximum temperature as measured by separating the low temperature exothermic part and the high temperature exothermic part from each other by a proper measure. Incidentally, in this description, the maximum temperature in the case of exhibiting a preferred range regarding the maximum temperature is a maximum temperature as measured by this JIS method.

In the invention, examples of a method for making a maximum temperature as generated by the high temperature exothermic part of the heat generating body higher than a maximum temperature as generated by the low temperature exothermic part and making a maximum temperature as generated by the middle sectional exothermic part laid therebetween include (1) a method in which plural sectional exothermic parts having substantially the same area are disposed at prescribed intervals, thereby utilizing a difference of the heat insulating effect between the central part and the end part. Examples of other methods include (2) a method in which in the respective sectional exothermic parts, the planar area is made different; (3) a method in which the amount of air of an air-permeable sheet for covering the heat generating body is made different; and (4) a method in which the kind and/or the composition of the heat generating body is made different. Also, these methods may be properly combined.

The foregoing method (1) utilizes the matter that the higher the heat insulating effect, the higher the maximum temperature. This method has such an advantage that the maximum temperature of the both can be made different without changing a basis weight of the heat generating composition molded body.

On the other hand, in the case of adding a flocculant aid, a flocculant, an agglomeration aid, a dry binding material, a dry binding agent, a dry binder, a sticky raw material, a thickener or an excipient, or determining the thickness of a compressed body by pressure while taking a pressure as a standard, exothermic characteristics, especially exothermic rising properties are remarkably deteriorated so that it takes a long period of time to reach a desired temperature. Thus, it is difficult to produce a practically useful heat generating body.

Furthermore, though a heat generating body of a short time type could be prepared, it is difficult to prepare a compressed body which is capable of continuing the heat generation at a proper temperature for one hour or more. When the heat generating body is more compressed, the shape holding properties are improved. However, the exothermic rising properties become worse, the maximum exothermic temperature is lowered, and the exothermic time becomes short. In particular, in a heat generating body in which a crosslinking agent, a plasticizer, etc. is added to enhance flexibility, for the purpose of increasing the exothermic characteristics, there was the case where it must be unavoidably used in an opened state where the air permeability is not adjusted.

It was difficult to embody a heat generating body which is able to achieve mild warming over a long period of time by adjusting the air permeability by an air-permeable film or the like.

The heat generating composition molded body of the invention is a compressed body which is not flexible but which after compression, is capable of causing heat generation upon contact with air without adding water or an aqueous solution containing a metal salt to the compressed body. The heat generating composition molded body of the invention is free from staining of the environment by a carbon component, etc., has excellent exothermic characteristics and shape holding properties, is sufficiently durable against processing into a heat generating body and is able to produce various heat generating bodies including from heat generating bodies having a single exothermic part to heat generating bodies having an exothermic part provided with plural chambers provided at intervals.

That is, heat generating composition molded bodies of various shapes including from a curved shape to a linear shape, various sizes including from a small size to a large size, various thicknesses including from an ultra-thin thickness to a thick thickness, or various widths including from a thin width to a wide width can be prepared. Following this, exothermic parts and heat generating bodies of various similar shapes or sizes can be produced.

Examples thereof include a triangular shape, a pyramidal shape, a star-like shape, a conical shape, a spherical shape, a square shape, a rectangular shape, a parallelepiped shape of rectangle, a cylindrical shape, and an elliptical shape. It can be set up such that a widest width is from 0.5 cm to 5 cm; a thinnest thickness is more than 0.2 cm and up to 1 cm; and a longest length is from 1.5 cm to 10 cm.

Furthermore, a concave or the like may be present in the central part, etc. of the heat generating composition molded body.

Here, since the moldable heat generating composition having a water mobility value of from 0.01 to 20 of the invention contains surplus water, when a pressure is applied, the particles easily come into contact with each other so that the particles are fixed due to a surface tension of water. Furthermore, since the heat generating composition molded body of the invention keeps a thickness of from 45 to 99.5% of the thickness at the time of molding, namely the die thickness, the water necessary for the heat generation is not lost at the time of compression, and after compression, a sufficient duration of heat generation can be secured without need of activation by adding water or brine through on-line, etc.

Furthermore, the thickness to the die thickness after compression, which is a compression rate, is usually from 50 to 99.5%, preferably from 60 to 95.5%, more preferably from 50 to 95%, further preferably from 65 to 95%, and still further preferably from 65 to 90% of the die thickness.

Furthermore, the matter of surplus water having a water mobility value of from 0.01 to 20 as needed in the invention could not be predicted. That is, the surplus water covers the powder surface and functions as a barrier so that the exothermic reaction is remarkably dropped, and there was considered a possibility that according to circumstances, a prescribed amount of water must be removed from the heat generating composition.

On the contrary, the surplus water having a water mobility value of from 0.01 to 20 assists binding of carbon and iron because the amount of the surplus water is appropriate, whereby not only a hard compressed body was generated without excessively diluting the heat generating composition, but also a function to cause an exothermic reaction immediately after contact with air was given to the heat generating composition.

According to the invention, by using surplus water having a water mobility value of from 0.01 to 20 in the compression operation, carbon dusts are reduced; various problems on the production are dissolved; the production line speed and the precision of filling weight are increased; fluidity of the heat generating composition is improved; non-uniformity of the heat generating composition within the completed exothermic part is removed; the performance of the completed exothermic part is improved; necessity of a special device and circumferences is eliminated; and required labors, danger on health and safety and production costs of the whole are remarkably lowered by all of them.

An exothermic part or a heat generating body into which the heat generating composition molded body which is produced by the production process of the invention and is capable of causing heat generation on the basis of a specified oxidation chemical reaction of iron is incorporated has specified physical dimensions and shape characteristic and gives long-term durable exothermic properties and improved temperature control properties.

The sectional exothermic part contains a wet type compressed particulate exothermic substance or a heat generating composition; this wet type compressed particulate exothermic substance or heat generating composition molded body substantially fills an effective capacity of the exothermic part within the sectional exothermic part, thereby reducing a surplus spacial capacity which may be possibly present and minimizing an ability of the exothermic substance to move within the exothermic part. This is achieved without applying a working pressure to the exothermic part wall. Since such an exothermic part has flexible physical dimensions, by incorporating it into a throwaway body worn implement, etc., it is possible to adapt to an external form of every body and to achieve warming of the body conveniently, comfortably and constantly.

The foregoing method (2) utilizes the matter that the larger the planar area, the higher the maximum temperature. This method has such an advantage that the maximum temperature of the both can be made different without changing a basis weight or thickness of the heat generating composition molded body or the heat generating composition molded body.

By applying the foregoing method (1) to the foregoing method (2), the maximum temperature of the both can be made different, too. By making the area of the high temperature exothermic part larger than the area of the middle temperature exothermic part and making the area of the middle temperature exothermic part larger than the area of the low temperature exothermic part, it is possible to make the maximum temperature as generated by the high temperature exothermic part larger than the maximum temperature as generated by the low temperature exothermic part.

The foregoing method (3) utilizes the matter that the larger the amount of air of an air-permeable sheet for covering the heat generating composition molded body or the heat generating composition molded body, the higher the maximum temperature. By making the amount of air of the air-permeable sheet of the high temperature sectional exothermic part larger than the amount of air of the air-permeable sheet of the low temperature sectional exothermic part, it is possible to make the maximum temperature as generated by the high temperature sectional exothermic part larger than the maximum temperature as generated by the low temperature sectional exothermic part or the middle temperature sectional exothermic part.

In general, the heat generating body of the invention is not limited with respect to the matter that an iron powder is used as the major component in a throwaway body warmer, etc. According to the foregoing method (3), the maximum temperature is adjusted by adjusting the feed amount of air to the heat generating composition molded body or the heat generating composition molded body, more specifically to an iron powder capable of causing heat generation by an oxidation reaction or the like. For that reason, the air-permeable sheet is not limited with respect to its disposition place or material quality or the like so far as it is a sheet which is able to adjust the feed amount of air to the heat generating composition molded body or the heat generating composition molded body. For example, in the case where the heat generating composition molded body or the heat generating composition molded body is interposed and fixed between a pair of a front surface sheet and a back surface sheet, either one of the both sheets may be formed of an air-permeable sheet, thereby making the amount of air of this air-permeable sheet different among the low temperature sectional exothermic part, the middle temperature exothermic part and the high temperature sectional exothermic part. Also, the both sheets may be formed of an air-permeable sheet, thereby making the amount of air of the both sheets different among the low temperature sectional exothermic part, the middle temperature sectional exothermic part and the high temperature sectional exothermic part. Furthermore, as the air-permeable sheet, sheets of various material qualities which are conventionally used for throwaway body warmers can be used. The air-permeable sheet may be formed of a laminated sheet.

Incidentally, the amount of air of the air-permeable sheet is defined in terms of a moisture permeability by the Lyssy method.

Examples of the foregoing method (4) include a method in which the kind of an iron powder which is the major component of the heat generating composition molded body or the heat generating composition molded body is made different; and a method in which the contents of one kind or two or more kinds of components of the heat generating composition molded body or the heat generating composition molded body, for example, an iron powder, a water retaining agent, water, and salt in the heat generating composition molded body or the heat generating composition molded body are made different among the low temperature sectional exothermic part, the middle temperature sectional exothermic part and the high temperature sectional exothermic part.

In the invention, it is regulated that the maximum temperature as generated by the high temperature sectional exothermic part is 2° C. or higher, and preferably from 5 to 10° C. higher than the maximum temperature as generated by the low temperature sectional exothermic part.

When a temperature difference between the low temperature sectional exothermic part and the high temperature sectional exothermic part is 2° C. or more, it becomes possible to achieve effective warming while especially applying the mutual characteristics among the low temperature sectional exothermic part, the middle temperature sectional exothermic part and the high temperature sectional exothermic part.

Furthermore, it is regulated that the maximum temperature as generated by the low temperature exothermic part is preferably from 35 to 50° C., and especially preferably from 37 to 42° C.; and that the maximum temperature as generated by the middle temperature exothermic part is preferably from 37 to 60° C., and especially preferably from 40 to 50° C. Also, it is regulated that the maximum temperature as generated by the high temperature exothermic part is preferably from 40 to 70° C., and especially preferably from 45 to 55° C.

When the maximum temperature as generated by the low temperature exothermic part is lower than 35° C., the warming effect by the low temperature exothermic part is hardly expected under the usual circumstances. The middle temperature exothermic part fills a temperature difference between the low temperature exothermic part and the high temperature exothermic part so that it becomes possible to warm a wide range with a gradual temperature inclination. By combining the low temperature exothermic part, the middle temperature exothermic part and the high temperature exothermic part on demand, it is possible to warm a wide range with a temperature inclination rich in variety and to create a temperature stimulus, if desired.

When the maximum temperature exceeds 70° C., an unwell feeling is liable to be generated due to a high temperature depending upon the area of the high temperature exothermic part.

A raw material of the substrate or covering material is not limited so far as it functions as an accommodating bag of the heat generating composition. Usually, raw materials which are used in chemical body warmers or heat generating bodies can be used. Examples of the raw material include air-impermeable raw materials, air-permeable raw materials, water absorptive raw materials, non-water absorptive raw materials, non-extensible raw materials, extensible raw materials, stretchable raw materials, non-stretchable raw materials, foamed raw materials, non-foamed raw materials, non-heat sealable raw materials, and heat sealable raw materials. The raw material can be properly used depending upon a desired utility in a desired form such as films, sheets, non-woven fabrics, woven fabrics, and composites thereof.

In general, the substrate is made of an air-impermeable film or sheet, and the covering material is made of an air-permeable film or sheet or non-woven fabric, and vice versa. The both may be air-permeable. As the underlay material, an air-permeable underlay material and an air-impermeable underlay material may be used for different purposes.

The packaging material of the accommodating bag may be of a single-layered structure or multilayered structure, and its structure is not limited. Furthermore, though the packaging material is composed of at least a substrate and a covering material, a packaging material for laminating the heat generating composition molded body is the substrate, and a packaging material for covering on the heat generating composition molded body is the covering material regardless of whether the packaging material is air-permeable or air-impermeable. An embodiment of a multilayered structure in which an air-impermeable packaging material is the substrate and an air-permeable packaging material is the covering material will be hereunder described as one example. That is, in this embodiment, the substrate is made of layer A/layer B, layer A/layer B/layer C, or layer A/layer B/layer C/layer D; and the covering material is made of layer F/layer G, layer E/layer F/layer G, or layer F/layer H/layer G. Examples of the layer A include thermoplastic resin films (for example, polyethylene), heat seal layers (for example, polyethylene and EVA), and water absorptive papers; examples of the layer B include non-woven fabrics of a thermoplastic resin (for example, nylons), non-water absorptive papers, water absorptive papers, thermoplastic resin films (for example, polyethylene films, polypropylene films, polyester films, and polyamide (for example, nylons) films), wicks (for example, non-water absorptive papers and water absorptive papers); examples of the layer C include adhesive layers, non-water absorptive papers, water absorptive papers, thermoplastic resin films (for example, polyethylene), non-slip layers, and non-woven fabrics of a thermoplastic resin (for example, polyesters and nylons); examples of the layer D include separators, thermoplastic resin films (for example, polyethylene), and non-woven fabrics; examples of the layer E include heat seal layers; examples of the layer F include porous films or perforated films made of a thermoplastic resin (for example, polyethylene), films made of a thermoplastic resin (for example, polyethylene), non-water absorptive papers, and water absorptive papers; examples of the layer G include non-woven fabrics of a thermoplastic resin (for example, polyesters and nylons); and examples of the layer H include non-water absorptive papers and water absorptive papers. Examples of the substrate or covering material include heat seal layer made of polyethylene obtained by using a metallocene catalyst/polypropylene film, polyethylene-made heat seal layer/polypropylene film, EVA-made heat seal layer/polypropylene film, EVA-made heat seal layer/polypropylene film/adhesive layer/separator, EVA-made heat seal layer/polyethylene film/nylon non-woven fabric, non-woven fabric/porous film, heat seal layer made of polyethylene obtained by using a metallocene catalyst/polyethylene film/nylon non-woven fabric, heat seal layer made of polyethylene obtained by using a metallocene catalyst/polypropylene film/polypropylene non-woven fabric, non-woven fabric/(paper and/or perforated (provided by a needle or laser) film)/porous film, non-woven fabric/(paper and/or porous film)/perforated (provided by a needle or laser) film, and non-woven fabric/(paper and/or porous film)/non-woven fabric. A method for laminating the respective layers is not limited. The respective layers may be directly laminated; the respective layers may be laminated via an air-permeable adhesive layer or a laminating agent layer; and the respective layers may be laminated by hot melt extrusion or the like. Furthermore, in the invention, it is to be noted that polyethylene produced by using a metallocene catalyst is also included in the polyethylene.

For example, in the case of laminating the foregoing raw material such as non-woven fabrics and porous films via an air-permeable sticky layer, examples of a method for forming the air-permeable sticky layer include a method in which a sticky substance is fibrillated by an appropriate system such as a curtain spray system, a melt blow system or a slot spray system for blowing and spreading a sticky substance via hot air under heat melting and spread and accumulated on an appropriate supporting substrate made of a porous film, an air-permeable substrate, a separator, etc., thereby forming a porous sticky layer.

A thickness of each of the substrate, the covering material, the underlay material, and the raw material constituting the same varies depending upon the utility and is not limited. The thickness is usually from 5 to 5,000 µm, preferably from 10 to 500 µm, and more preferably from 20 to 250 µm.

The air-impermeable raw material is not limited so far as it is air-impermeable. Examples thereof include films, sheets or coatings made of a polymer (for example, polyethylene, polypropylene, nylons, polyacrylates, polyesters, polyvinyl alcohols, and ethylene-vinyl acetate copolymers) and laminates thereof with a metal (including a semiconductor) compound (for example, silicon oxide) or composite raw materials using the same.

Of the foregoing air-impermeable raw materials, examples of a film having high air impermeability include films provided with a single layer or multiple layers of a thin film having a metal including a semiconductor or a compound thereof provided on an air-impermeable raw material film. Examples of the metal including a semiconductor include silicon, aluminum, and alloys or mixtures containing such a metal. Examples of the metal (including a semiconductor) compound include oxides, nitrides and oxynitrides of the foregoing metals or alloys or mixtures. Examples of the layer include silicon oxide layers, aluminum oxide layers, and silicon oxynitride layers; layers obtained by laminating an arbitrary layer of these layers on a polyester-made film; and layers obtained by further laminating a stretched polyolefin film (for example, a biaxially stretched polypropylene film) thereon.

The air-permeable raw material is not limited so far as it is air-permeable. Examples thereof include air-permeable films (for example, porous films and perforated films); materials having air permeability by themselves (for example, papers and non-woven fabrics); materials prepared by laminating at least one of papers and air-permeable films and non-woven fabrics so as to have air permeability; materials prepared by providing an air-impermeable packaging material comprising a non-woven fabric having a polyethylene film laminated thereon with fine pores by using a needle, etc. so as to have air permeability; non-woven fabric whose air permeability is controlled by laminating a fiber and heat bonding under pressure; porous films; and materials prepared by sticking a non-woven fabric onto a porous film. The "perforated film" as referred to herein is a film prepared by providing an air-impermeable film (for example, polyethylene films) with fine pores by using a needle so as to have air permeability.

The air permeability is not limited so far as the heat generation can be kept. In the case of use in usual heat generation, the air permeability is usually from 50 to 10,000 $g/m^2/24$ hr, preferably from 70 to 5,000 $g/m^2/24$ hr, more preferably from 100 to 2,000 $g/m^2/24$ hr, and further preferably from 100 to 700 $g/m^2/24$ hr in terms of moisture permeability by the Lyssy method.

When the moisture permeability is less 50 $g/m^2/24$ hr, the heat value is small and a sufficient thermal effect is not obtained, and therefore, such is not preferable. On the other hand, when it exceeds 10,000 $g/m^2/24$ hr, the exothermic temperature is high so that a problem in safety may possibly be generated, and therefore, such is not preferable. However, there is no limitation even when the moisture permeability exceeds 10,000 $g/m^2/24$ hr depending upon the utility, or even in the use at a moisture permeability closed to the open system, according to circumstances.

The stretchable packaging material is not particularly limited so far as it is stretchable. That is, it is only required that the stretchable packaging material is stretchable as a whole. The stretchable packaging material may be formed of a single material or a composite material of stretchable substrates or a combination of a stretchable substrate and a non-stretchable substrate.

Examples of the stretchable packaging material include single materials (for example, natural rubbers, regenerated rubbers, synthetic rubbers, elastomers, and stretchable shape memory polymers) and mixtures thereof, mixed materials or blended materials of such a stretchable raw material and a non-stretchable raw material or fabrics constituted of a combination of these materials, films, yarns, strands, ribbons, tapes, and stretchable films with a scrim structure.

The porous film is not limited and can be properly selected among porous films obtained by stretching a film made of a polyolefin based resin (for example, polyethylene, linear low density polyethylene, and polypropylene) or a fluorine based resin (for example, polytetrafluoroethylene) and a filler.

The non-woven fabric is not limited. Single non-woven fabrics of a single fiber or composite fiber made of a material such as rayon, nylons (polyamides), polyesters, polyacrylates, polypropylene, vinylon, polyethylene, polyurethane, cupra, cotton, cellulose, and pulp, or laminates of blended or accumulated fiber layers of such fibers are useful. Furthermore, from the standpoint of production process, dry non-woven fabrics, wet non-woven fabrics, spunbonds, spunlaces, and the like can be used. Non-woven fabrics made of a composite fiber having a core-sheath structure are also useful. A non-woven fabric in the side which is brought into contact with the skin is preferably a napping (fluffy) non-woven fabric. Also, stretchable non-woven fabrics and non-stretchable non-woven fabrics are useful.

The water absorptive raw material is not particularly limited so far as it is a water absorptive film or sheet.

The water absorptive raw material is not particularly limited so far as it has water absorption properties consequently regardless of whether or not the raw material has water absorption properties by itself.

Specific examples thereof include water absorptive foamed films or sheets having water absorption-properties (for example, foamed bodies of water absorptive foamed polyurethane, etc.) or papers, non-woven fabrics or woven fabrics formed of a fiber having water absorption properties, non-woven fabrics or woven fabrics containing a fiber having water absorption properties, and water absorptive materials such as water absorptive porous films or sheets. Besides, there are enumerated materials in which regardless of the presence or absence of water absorption properties, a water absorbing agent is contained, impregnated, kneaded, transferred or carried on a foamed film or sheet, a non-woven fabric, a woven fabric or porous film or sheet, thereby imparting or increasing water absorption properties; and materials in which regardless of the presence or absence of water absorption properties, a water absorptive raw material such as water absorptive foamed films or sheets, papers, non-woven fabrics, woven fabrics, and porous films or sheets as cut in a planar shape according to the invention is attached to one side or both sides of the material according to the invention, thereby imparting water absorption properties.

In particular, in the heat generating body of the invention, for the purpose of forming the plane which is brought into contact with the skin into a comfortable plane by imparting water absorption properties against sweat, etc., in order that in the case of sweating, the sweat is absorbed, it is preferable that a packaging material in the plane which is brought into contact with the skin is constituted of a packaging material using a non-woven fabric or a woven fabric containing, as the major component, a water absorptive fiber having a water retention of 20% or more. Examples of the water absorptive fiber having a water retention of 20% or more include cottons, silks, hemps, wools, polyacrylonitrile based synthetic fibers, polyamide based synthetic fibers, polyvinyl alcohol based synthetic fibers, acetate fibers, triacetate fibers, and regenerated fibers. In addition, non-woven fabrics having a highly water absorptive polymer held in a non-woven fabric can be used as the non-woven fabric having excellent water absorption properties. Incidentally, non-woven fabrics or woven fabrics containing such a fiber as the major component are relatively good with respect to the feeling against the skin.

In addition, highly water absorptive packaging materials having high absorption properties of sweat can be used as the packaging material. Examples thereof include non-woven fabrics containing a fiber whose surface is coated with a highly water absorptive resin, non-woven fabrics containing a hollow fiber having a number of fine pores on the surface thereof, and non-woven fabrics containing a fiber having a capillary action by forming a number of pouches or plural layers in the cross-sectional shape.

Besides, non-woven fabrics or films having a water absorptive inorganic compound held on a non-sticky surface of a packaging material can be used. Examples thereof include non-woven fabrics resulting from holding a powder (for example, diatomaceous earth, zeolite, and silica gel) on a non-woven fabric and films resulting from holding a relatively large amount of a powder (for example, silica and alumina) on a synthetic resin (for example, polyethylene).

The heat generating composition molded body or the heat generating composition molded body of the invention contains, as essential components, an iron powder, a carbon component, a reaction accelerator and water.

Examples of the production process of a heat generating body using the thus produced heat generating composition molded body include a production process in which the heat generating composition molded body is laminated on a substantially planar substrate, a covering material is put thereon, and the periphery of the heat generating composition molded body is heat sealed; and a production process in which the heat generating composition molded body is filled in a pocket of a pocket-provided packaging material, other packaging material is put thereon, and the periphery of the pocket is heat sealed. In the heat generating composition molded body, the shape necessary for filling it in a pocket can be thoroughly kept.

Furthermore, in the heat generating body of the invention which is composed of an exothermic part having plural sectional exothermic parts according to the invention, the distance between the sectional exothermic parts is flexible and the heat generating body is high in flexibility so that it can be fitted to any curved surface parts of a human body. Furthermore, since the exothermic characteristics per unit weight are excellent, for the purpose of realizing exothermic characteristics comparable to the conventional heat generating bodies, the amounts of the exothermic agent components may be made small. As a result, it is possible to make the heat generating body light or thin so that the feeling for use is remarkably improved.

As other production process of a heat generating body using the heat generating composition molded body according to the invention, the heat generating body can be produced by holding a magnetic iron-containing heat generating composition molded body in a prescribed flat place of a substrate by singly using magnetism as generated from a magnet in the bottom part of a die or using the magnetism together with a reduce pressure, placing a covering material on the substrate such that a compressed body is positioned between these two sheets, and subsequently sealing the compressed body between the substrate and the covering material.

Furthermore, according to another process, the heat generating body can be produced by holding a magnetic iron-containing heat generating composition molded body in a pocket as formed in advance in a substrate or a pocket as formed under a reduced pressure by singly using magnetism as generated from a magnet in the bottom part of a die or using the magnetism together with a reduce pressure, placing a covering material on the substrate such that a compressed body is positioned between these two sheets, and subsequently sealing the compressed body between the substrate and the covering material.

The heat generating composition is not limited so far as it is a heat generating composition which contains, as essential components, an iron powder, a carbon component, a reaction accelerator and water, does not contain a flocculant aid, a flocculant, an agglomeration aid, a dry binding material, a dry binding agent, a dry binder, a sticky raw material, a thickener and an excipient, contains surplus water so as to have a water mobility value of from 0.01 to 20, has moldability due to the surplus water, with the water in the heat generating composition not functioning as a barrier layer, and is capable of causing an exothermic reaction upon contact with air.

In addition, if desired, at least one member selected from additional components consisting of a water retaining agent, a water absorptive polymer, a pH adjusting agent, a hydrogen formation inhibitor, an aggregate, a fibrous material, a functional substance, a surfactant, an organosilicon compound, a pyroelectric substance, a moisturizer, a fertilizer component, a hydrophobic polymer compound, a heat generating aid, a metal other than iron, a metal oxide other than iron oxide, an acidic substance, and a mixture thereof may be further added to the heat generating composition.

Furthermore, in the heat generating composition of the invention or the like, although there is no particular limitation for the compounding ratio thereof, it is preferred to select the compounding ratio such that the amount of the reaction accelerator is from 1.0 to 50 parts by weight, the amount of water is from 1.0 to 60 parts by weight, the amount of the carbon component is from 1.0 to 50 parts by weight, the amount of the water retaining agent is from 0.01 to 10 parts by weight, the water absorptive polymer is from 0.01 to 20 parts by weight, the amount of the pH adjusting agent is from 0.01 to 5 parts by weight, and the amount of the hydrogen formation inhibitor is from 0.01 to 12 parts by weight, respectively based on 100 parts by weight of the iron powder; and that the heat generating composition has a water mobility value of from 0.01 to 20.

In addition, the following components may be added in compounding ratios as described below to the iron powder to the heat generating composition. That is, the amount of the metal other than iron is from 1.0 to 50 parts by weight, the amount of the metal oxide other than iron oxide is from 1.0 to 50 parts by weight, the amount of the surfactant is from 0.01 to 5 parts by weight, the amount of each of the hydrophobic polymer compound, the aggregate, the fibrous material, the functional substance, the organosilicon compound and the pyroelectric substance is from 0.01 to 10 parts by weight, the amount of each of the moisturizer, the fertilizer component and the heat generating aid is from 0.01 to 10 parts by weight, and the amount of the acidic substance is from 0.01 to 1 part by weight based on 100 parts by weight of the iron powder. Incidentally, a magnetic material may further be compounded, and its compounding ratio may be properly determined depending upon the desire.

Incidentally, these compounding ratios can also be applied in a reaction mixture and a heat generating mixture. Furthermore, a water mobility value of the reaction mixture is usually less than 0.01.

As the water, one from a proper source may be employed. Its purity and kind and the like are not particularly limited.

In the case of the heat generating composition, the content of water is preferably from 1 to 70% by weight, more preferably from 1 to 60% by weight, further preferably from 7 to 60% by weight, still further preferably from 10 to 50% by weight, and even further preferably from 20 to 50% by weight of the heat generating composition.

Furthermore, in the case of the reaction mixture or heat generating mixture prior to the contact treatment with an oxidizing gas, the content of water is preferably from 0.5 to 20% by weight, more preferably from 1 to 20% by weight, further preferably from 3 to 20% by weight, and still further preferably from 4 to 15% by weight of the reaction mixture or heat generating mixture.

The carbon component is not particularly limited so far as it contains carbon as a component. Examples thereof include carbon black, graphite, active carbon, carbon nanotubes, carbon nanohorns, and flullerenes. Carbon which has become conductive by doping or the like is also employable. There are enumerated active carbons as prepared from coconut shell, wood, charcoal, coal, bone carbon, etc. and carbons as prepared from other raw materials such as animal products, natural gases, fats, oils, and resins. In particular, active carbons having an adsorption retaining ability are preferable.

Furthermore, it is not always required that the carbon component is present alone. In the case where an iron powder containing the carbon component and/or covered by the carbon component is used in the heat generating composition, it is to be noted that the heat generating composition contains the carbon component even though the carbon component is not present alone.

The reaction accelerator is not particularly limited so far as it is able to promote the reaction of the heat generating substance. Examples thereof include metal halides, nitrates, acetates, carbonates, and metal sulfates. Examples of metal halides include sodium chloride, potassium chloride, magnetic chloride, calcium chloride, ferrous chloride, ferric chloride, sodium bromide, potassium bromide, ferrous bromide, ferric bromide, sodium iodide, and potassium iodide. Examples of nitrates include sodium nitrate and potassium nitrate. Examples of acetates include sodium acetate. Examples of carbonates include ferrous carbonate. Examples of metal sulfates include potassium sulfate, sodium sulfate, and ferrous sulfate.

The water retaining agent is not limited so far as it is able to retain water. Examples thereof include porous materials derived from plants having high capillary function and hydrophilicity such as wood meal, pulp powder, active carbon, saw dust, cotton cloth having a number of cotton fluffs, short fiber of cotton, paper dust, and vegetable materials, water-containing magnesium silicate based clay minerals such as active clay and zeolite, pearlite, vermiculite, silica based porous substances, coralline stone, and volcanic ash based substances (for example, terraballoon, shirasu balloon, and taisetsu balloon). In order to increase a water retaining ability and enhance a shape holding ability of such a water retaining agent, the water retaining agent may be subjected to a processing treatment such as baking and/or pulverization.

The water absorptive polymer is not particularly limited so far as it is a resin having a crosslinking structure and having a water absorption magnification of ion-exchanged water of 3 times or more of the dead weight. Furthermore, a water absorptive polymer the surface of which is crosslinked may be employed. Conventionally known water absorptive polymers and commercial products may also be employed.

Examples of the water absorptive polymer include poly(meth)acrylic acid crosslinked materials, poly(meth)acrylic acid salt crosslinked materials, sulfonic group-containing poly(meth)acrylic ester crosslinked materials, polyoxyalkylene group-containing poly(meth)acrylic ester crosslinked materials, poly(meth)acrylamide crosslinked materials, crosslinked materials of a copolymer of a (meth)acrylic acid salt and a (meth)acrylamide, crosslinked materials of a copolymer of a hydroxyalkyl(meth)acrylate and a (meth)acrylic acid salt, polydioxolane crosslinked materials, crosslinked polyethylene oxide, crosslinked polyvinylpyrrolidone, sulfonated polystyrene crosslinked materials, crosslinked polyvinylpyridine, saponification products of a starch-poly(meth)acrylonitrile graft copolymer, starch-poly(meth)acrylic acid (salt) graft crosslinked copolymers, reaction products of polyvinyl alcohol and maleic anhydride (salt), crosslinked polyvinyl alcohol sulfonic acid salts, polyvinyl alcohol-acrylic acid graft copolymers, and polyisobutylene maleic acid (salt) crosslinked polymers. These water absorptive polymers may be used alone or in combination with two or more kinds thereof.

Of these water absorptive polymers, water absorptive polymers having biodegradation properties are not limited so far as they are a biodegradable water absorptive polymer. Examples thereof include polyethylene oxide crosslinked materials, polyvinyl alcohol crosslinked materials, carboxymethyl cellulose crosslinked materials, alginic acid crosslinked materials, starch crosslinked materials, polyamino acid crosslinked materials, and polylactic acid crosslinked materials.

The pH adjusting agent is not limited so far it is able to adjust the pH. Examples thereof include alkali metal weak acid salts and hydroxides and alkaline earth metal weak acid salts and hydroxides such as $Na_2CO_3$, $NaHCO_3$, $Na_3PO_4$, $Na_2HPO_4$, $Na_5P_3O_{10}$, $NaOH$, $KOH$, $Ca(OH)_2$, $Mg(OH)_2$, and $Ca_3(PO_4)_2$.

The hydrogen formation inhibitor is not limited so far as it is able to inhibit the formation of hydrogen. Examples thereof include one member or two or more members selected from the group consisting of sulfur compounds, oxidizing agents, alkaline substances, sulfur, antimony, selenium, phosphorus, and tellurium. Incidentally, examples of sulfur compounds include compounds with an alkali metal or an alkaline earth metal, metal sulfides such as calcium sulfide, metal sulfites such as sodium sulfite, and metal thiosulfates such as sodium thiosulfate.

Examples of the oxidizing agent include nitrates, oxides, peroxides, halogenated oxygen acid salts, permanganates, and chromates.

The aggregate is not limited so far as it is useful as a filler and/or is useful for making the heat generating composition porous. Examples thereof include fossilized coral (for example, coral fossil and weathered coral fossil), bamboo charcoal, bincho charcoal, silica-alumina powders, silica-magnesia powders, kaolin, crystalline cellulose, colloidal silica, pumice, silica gel, silica powders, mica powders, clays, talc, synthetic resin powders or pellets, foamed synthetic resins such as foamed polyesters or polyurethanes, diatomaceous earth, alumina, and cellulose powder. Incidentally, it is to be noted that kaolin and crystalline cellulose are not contained in the heat generating composition of the invention.

The fibrous material is an inorganic fibrous material and/or an organic fibrous material. Examples thereof include rock wool, glass fibers, carbon fibers, metal fibers, pulps, papers, non-woven fabrics, woven fabrics, natural fibers such as cotton and hemp, regenerated fibers such as rayon, semi-synthetic fibers such as acetates, synthetic fibers, and pulverized products thereof.

The functional substance is not limited so far as it is a substance having any function. Examples thereof include at least one member selected from minus ion emitting substances and far infrared ray radiating substances. The minus ion emitting substance is not limited so far as it emits a minus ion as a result either directly or indirectly, and examples thereof include ferroelectric substances such as tourmaline, fossilized coral, granite, and calcium strontium propionate, and ores containing a radioactive substance such as radium and radon. The far infrared ray radiating substance is not limited so far as it radiates far infrared rays. Examples thereof include ceramics, alumina, zeolite, zirconium, and silica.

The surfactant includes anionic surfactants, cationic surfactants, nonionic surfactants, and ampholytic surfactants. Especially, nonionic surfactants are preferable, and examples thereof include polyoxyethylene alkyl ethers, alkylphenol-ethylene oxide adducts, and higher alcohol phosphoric acid esters.

The organosilicon compound is not limited so far as it is a compound having at least an Si—O—R bond and/or an Si—N—R bond and/or an Si—R bond. The organosilicon compound is in the form of a monomer, a lowly condensed product, a polymer, etc. Examples thereof include organosilane compounds such as methyltriethoxysilane; and dimethylsilicone oil, polyorganosiloxane, or silicone resin compositions containing the same.

The pyroelectric substance is not limited so far as it has pyroelectricity. Examples thereof include tourmaline, hemimorphic ores, and pyroelectric ores. Tourmaline or achroite which is a kind of tourmaline is especially preferable. Examples of the tourmaline include dravite, schorl, and elbaite.

The moisturizer is not limited so far as it is able to hold moisture. Examples thereof include hyaluronic acid, collagen, glycerin, and urea.

The fertilizer component is not limited so far as it is a component containing at least one of three elements of nitrogen, phosphorus and potassium. Examples thereof include a bone powder, urea, ammonium sulfate, calcium perphosphate, potassium chloride, and calcium sulfate.

The hydrophobic polymer compound is not limited so far as it is a polymer compound having a contact angle with water of 40° or more, preferably 50° or more, and more preferably 60° or more in order to improve the draining in the composition. The shape of the hydrophobic polymer compound is not limited, and examples thereof include powdery, particulate, granular, and tablet shapes. Examples of the hydrophobic polymer compound include polyolefins such as polyethylene and polypropylene, polyesters, and polyamides.

Examples of the heat generating aid include metal powders, metal salts, and metal oxides such as Cu, Mn, $CuCl_2$, $FeCl_2$, manganese dioxide, cupric oxide, triiron tetroxide, and mixtures thereof.

As the metal oxide other than iron oxide, any material can be employed so far as it does not hinder the oxidation of iron by an oxidizing gas, and examples thereof include manganese dioxide and cupric oxide.

The acidic substance may be any of an inorganic acid, an organic acid, or an acidic salt. Examples thereof include hydrochloric acid, sulfuric acid, nitric acid, acetic acid, oxalic acid, citric acid, malic acid, maleic acid, chloroacetic acid, iron chloride, iron sulfate, iron oxalate, iron citrate, aluminum chloride, ammonium chloride, and hypochlorous acid.

As the "iron powder" as referred to herein, usual iron powders, iron alloy powders and active iron powders such as iron powders comprising particles, a surface of each of which is at least partially covered with an oxygen-containing film, and iron alloy powders comprising particles, a surface of each of which is at least partially covered with an oxygen-containing film, are preferable. Incidentally, the "iron oxide film" as referred to herein is a film made of oxygen-containing iron such as iron oxide, hydroxide or oxyhydroxide. Furthermore, the "active iron powder" as referred to herein is a powder in which an iron oxide film is formed at least locally on the surface of an iron powder, from which an oxidation reaction promoting effect is obtained by a local cell as formed between an iron matrix and an iron oxide film or a pit inside and outside the iron oxide film.

The iron powder is not limited, and examples thereof include cast iron powders, atomized iron powders, electrolyzed iron powders, reduced iron powders, sponge iron powders, and iron alloy powders thereof. In addition, the iron powder may contain carbon or oxygen, and an iron powder containing 50% or more of iron and other metals may be employed. The kind of the metal which is contained as an alloy, etc. is not particularly limited so far as the iron component works as a component of the heat generating composition. Examples of such a metal include metals such as aluminum, manganese, copper, nickel, silicon, cobalt, palladium, and molybdenum, and semiconductors. The metal of the invention includes a semiconductor. Such a metal or alloy may be contained only in the surface or the interior, or may be contained in both the surface and the interior.

In the iron powder of the invention, the content of the metal other than iron is usually from 0.01 to 50% by weight, and preferably from 0.1 to 10% by weight based on the whole of the iron powder.

Examples of the iron powder having an oxygen-containing film on at least a part of the surface of the iron include:

(A) an active iron powder in which the surface of an iron component is at least partially oxidized, which is obtained by contact treating the essential components of the heat generating composition or the essential components to which acidic substances or other necessary components are added with an oxidizing gas, thereby partially oxidizing the iron component;

(B) an active iron powder in which the content of wustite is from 2 to 50% by weight in terms of an X-ray peak intensity ratio to iron;

(C) an iron powder having an iron oxide film having a thickness of 3 nm or more on the surface thereof; and (D) a mixture of an active iron powder and an iron powder other than an active iron powder.

With respect to (A), although the mechanism is not elucidated in detail, it is assumed that upon contact between the oxidizing gas and the components, not only an iron oxide film, namely, an oxygen-containing film is formed on the surface of the iron powder due to the oxidation of the components, especially the oxidation of the iron powder, but also the surface of active carbon is oxidized and/or the oxidized iron component is adhered, whereby hydrophilicity is imparted or improved, and coupling between the components or structurization takes place through the mediation of water.

That is, it is assumed that some kind of a change in the function occurs such that an iron oxide film is formed on the surface of the iron powder, the shape of the iron powder particle becomes irregular, a strain is generated due to the oxidation, or a water-containing pit is formed, whereby the iron powder is activated and exothermic rising properties are improved.

Furthermore, the case where magnetite ($Fe_3O_4$) is present in the iron oxide film is preferable because the conductivity is excellent, and the case where hematite ($Fe_2O_3$) is present in the iron oxide film is also preferable because the iron oxide film becomes porous. Moreover, it is assumed that the carbon component is oxidized on the surface thereof and becomes a carbon component which is rich in oxides on the surface thereof, whereby the hydrophilicity increases and the activity increases.

The thickness of the iron oxide film which is an oxygen-containing film covering the surface of the iron powder, as measured by the Auger electron spectroscopy, is usually 3 nm or more, preferably from 3 nm to 100 µm, more preferably from 30 nm to 100 µm, further preferably from 30 nm to 50 µm, still further preferably from 30 nm to 1 µm, even further preferably from 30 nm to 500 nm, and even still further preferably from 50 nm to 300 nm.

When the thickness of the oxygen-containing film of iron is 3 nm or more, the thickness of the oxygen-containing film of iron is able to exhibit a promoting effect of the oxidation reaction, and upon contact with an oxidizing gas such as air, is able to immediately initiate the oxidation reaction. When the thickness of the oxygen-containing film of iron is 100 µm or more, though the heat generation time may possibly be shortened, such is applicable depending upon the utility.

Furthermore, according to the active iron powder, by using a reaction mixture containing, as essential components, an iron powder, a reaction accelerator and water and having a water content of from 0.5 to 20% by weight and a water mobility value showing a surplus water content of less than 0.01, the reaction rate at the time of the contact treatment with an oxidizing gas can be raised, thereby achieving a time required for regulating a temperature rise of the reaction mixture at 1° C. or more within 10 minutes. By shortening a time required for arrival at a prescribed temperature or higher, proper activation can be achieved, and unnecessary oxidation on the iron powder can be prevented.

Furthermore, the heat generating composition prepared by adding a carbon component, etc. to a heat generating mixture as produced by contact treating the reaction mixture with an oxidizing gas or adjusting the water content so as to have a water mobility value of from 0.01 to 50 is properly tacky, has excellent moldability and is able to be applied with a molding method such as a force-through die molding method and a cast molding method, whereby heat generating bodies of various shapes can be produced. In particular, a heat generating composition having a water mobility value of from 0.01 to 20 is excellent because it initiates an exothermic reaction immediately after contacting with air, has excellent exothermic rising properties and has excellent moldability.

The contact treatment method of the reaction mixture with an oxidizing gas is not particularly limited so far as it is able to contact treat a reaction mixture containing, as essential components, an iron powder, a reaction accelerator and water and having a water content of from 0.5 to 20% by weight and a water mobility value of less than 0.01 with an oxidizing gas and regulate a temperature rise of the reaction mixture at 1° C. or more.

Specific examples thereof include:

(1) a process for producing a heat generating mixture containing an iron powder having an iron oxide film on the surface thereof by subjecting a reaction mixture of an iron powder, a reaction accelerator and water in an oxidizing gas atmosphere to a self-exothermic reaction, thereby partially oxidizing the iron powder;

(2) a process for producing a heat generating mixture by subjecting a reaction mixture of an iron powder, a reaction accelerator, an acidic substance and water in an oxidizing gas atmosphere to a self-exothermic reaction;

(3) a process for producing a heat generating mixture by subjecting a reaction mixture of an iron powder, a reaction accelerator, a carbon component and water in an oxidizing gas atmosphere to a self-exothermic reaction;

(4) a process for producing a heat generating mixture by subjecting a reaction mixture of an iron powder, a reaction accelerator, an acidic substance, a carbon component and water in an oxidizing gas atmosphere to a self-exothermic reaction;

(5) a process for producing a heat generating mixture containing a partially oxidized iron powder by carrying out the method as set forth above in any one of (1) to (4), wherein the reaction mixture or heat generating mixture as set forth above in any one of (1) to (4) contains a component other than the foregoing components;

(6) a process for producing a heat generating mixture by carrying out the method as set forth above in any one of (1) to (5) under circumstances heated so as to have temperature of at least 10° C. higher than the circumferential temperature;

(7) a process for producing a heat generating mixture by carrying out the method as set forth above in any one of (1) to (6) by blowing an oxidizing gas;

(8) a process for producing a heat generating mixture by carrying out the method as set forth above in (7) by blowing the oxidizing gas heated so as to have a temperature of at least 10° C. higher than the circumferential temperature;

(9) a process for producing a heat generating composition by carrying out the method as set forth above in any one of (1) to (8) by contact treating with an oxidizing gas until the temperature exceeds a maximum temperature which is a maximum point of temperature rise by the exothermic reaction;

(10) a process for producing a heat generating mixture by carrying out the method as set forth above in any one of (1) to (8) by contact treating with an oxidizing gas until the temperature exceeds a maximum temperature by the exothermic reaction and drops by at least 10 to 20° C. from the maximum temperature;

(11) a process for producing a heat generating composition by carrying out the method as set forth above in any one of (1) to (8) by contact treating with an oxidizing gas until the temperature exceeds a maximum temperature which is a maximum point of temperature rise by the exothermic reaction and after intercepting the oxidizing gas, holding it until the temperature of at least the reaction mixture drops by at least 10 to 20° C. from the maximum temperature; and

(12) a process for producing a heat generating mixture by heating the reaction mixture or heat generating mixture as set forth above in any one of (1) to (5) under oxidizing gas circumstances while regulating a temperature rise at 1° C. or more.

In addition, a heat generating mixture as prepared by adding other components to the heat generating mixture and further treating with an oxidizing gas may be employed.

Incidentally, the circumstances of the reaction mixture at the time of contact treatment with an oxidizing gas are not limited so far as the reaction mixture is brought into contact with an oxidizing gas under circumstances of 0° C. or higher and a temperature rise of the reaction mixture is regulated at 1° C. or more within 10 minutes. In the case where the contact treatment is carried out in an open system, the circumstances may be either the state that the reaction mixture is present in a lid-free vessel or the state that an oxidizing gas such as air comes into a vessel through an air-permeable sheet-like material such as non-woven fabrics.

Furthermore, the contact treatment with an oxidizing gas may be carried out with or without stirring in a fluidized or non-fluidized state and may be carried out in a batch or continuous system.

Examples of the final heat generating composition include:

1) a heat generating composition containing, as a heat generating composition raw material, a heat generating mixture produced in the process as set forth above in any one of (1) to (12);

2) a heat generating composition obtained by adding other components to the heat generating composition as set forth above in 1); and 3) a heat generating composition obtained by adjusting the water content of the heat generating composition as set forth above in 1) or 2).

The order of the timing of adding other components than the essential components and the timing of adjusting the water content is not limited.

Here, the water content in the reaction mixture and also the heat generating mixture prior to the treatment with an oxidizing gas is usually from 0.5 to 20% by weight, preferably from 1 to 15% by weight, more preferably from 2 to 10% by weight, further preferably from 3 to 10% by weight, and still further preferably from 6 to 10% by weight.

The temperature of the reaction mixture after the contact with an oxidizing gas is not limited so far as the temperature rise is regulated at 1° C. or more. The temperature of the reaction mixture after the contact with an oxidizing gas is preferably from 1 to 80° C., more preferably from 1 to 70° C., further preferably from 1 to 60° C., and still further preferably from 1 to 40° C.

The circumferential temperature at the time of contact between the reaction mixture and the oxidizing gas is not limited so far as the temperature of the reaction mixture is raised to a prescribed temperature or higher. The circumferential temperature at the time of contact between the reaction mixture and the oxidizing gas is preferably 0° C. or higher, more preferably from 0 to 250° C., further preferably from 10 to 200° C., still further preferably from 20 to 150° C., even further preferably from 25 to 100° C., and even still further preferably from 25 to 50° C.

The time of contact between the reaction mixture and the oxidizing gas is not limited so far as the time required for regulating a temperature rise at 1° C. or more is within 10 minutes. The time of contact between the reaction mixture and the oxidizing gas is preferably from one second to 10 minutes, more preferably from one second to 7 minutes, further preferably from one second to 5 minutes, still further preferably from 2 seconds to 5 minutes, even further preferably from 2 seconds to 3 minutes, and even still further preferably from 2 seconds to one minute.

The temperature of the oxidizing gas is not limited so far as the foregoing circumferential temperature is kept.

As the "oxidizing gas" as referred to herein, any gas can be used as the oxidizing gas so far as it is oxidizing. Examples thereof include an oxygen gas, air, and mixed gases of an inert gas (for example, a nitrogen gas, an argon gas, and a helium gas) and an oxygen gas. Although the mixed gas is not limited so far as it contains oxygen, mixed gases containing 10% or more of an oxygen gas are preferable, and of these, air is especially preferable. If desired, a catalyst such as platinum, palladium, iridium, and compounds thereof can also be used.

The oxidation reaction can be carried out under stirring in an oxidizing gas atmosphere optionally under a pressure and/or upon irradiation of ultrasonic waves.

The optimal condition of the oxidation reaction may be properly experimentally determined.

An amount of the oxidizing gas to be used is not limited but may be adjusted depending upon the kind of the oxidizing gas, the kind and particle size of the iron powder, the water content, the treatment temperature, the treatment method, and the like.

In the case of an open system, there is no limitation so far as a necessary amount of oxygen can be taken in. In order to prevent fly of the reaction mixture or contamination of dusts, etc., the system may be surrounded by an air-permeable raw material such as non-woven fabrics and woven fabrics. So far as the system is in an air-permeable state, it is to be noted that the system is an open system.

In the case where air is used in the system of blowing an oxidizing gas, for example, the amount of air is preferably from 0.01 to 1,000 L/min, more preferably from 0.01 to 100 L/min, and further preferably from 0.1 to 50 L/min per 200 g of the iron powder under one atmosphere. In the case of other oxidizing gas, the amount of the oxidizing gas may be converted on the basis of the case of air.

If desired, a peroxide may be added. Examples of the peroxide include hydrogen peroxide and ozone.

Here, so far as the iron powder is partially oxidized, the state of the reaction mixture or heat generating mixture at the time of the contact treatment with an oxidizing gas may be any of a standing state, a transfer state, or a fluidizing state by stirring, etc. and may be properly selected. Furthermore, the circumstances at the time of mixing the respective components of the reaction mixture, the heat generating mixture or the heat generating composition and at the time of the contact treatment with a mixed oxidizing gas at the time of adjusting the water content are not limited, and examples thereof include those in an oxidizing gas atmosphere and those in blowing of an oxidizing gas.

A method for measuring a temperature rise of the heat generating composition is as follows.

1) A heat generating composition is allowed to stand in a state that it is sealed in an air-impermeable outer bag for one hour under a condition that the circumferential temperature is 20±1° C.

2) A magnet is provided in the vicinity of a central part of the back side of a polyvinyl chloride-made supporting plate (3 mm in thickness×600 mm in length×600 mm in width) of a footed supporting table so as to cover a cavity shape of a molding die.

3) A temperature sensor is placed on the central part of the supporting plate.

4) A polyethylene film (25 μm in thickness×250 mm in length×200 mm in width) as provided with an adhesive layer having a thickness of about 80 μm is stuck onto the supporting plate via a sticky layer such that the center of the polyethylene film is positioned at the sensor.

5) The heat generating composition is taken out from the outer bag.

6) A template (250 mm in length×200 mm in width) having a cavity (80 mm in length×50 mm in width×3 mm in height) is placed above the central part of the polyethylene film; a sample is placed in the vicinity of the cavity; a force-in die plate is moved along the template; the sample is charged into the cavity while stuffing; and the sample is leveled while stuffing along the template plane (force-in die molding), thereby filling the sample in the die. Next, the magnet beneath the supporting plate is removed, and the temperature measurement is started.

With respect to the measurement of the exothermic temperature, the temperature is measured for 10 minutes at a measurement timing of 2 seconds using a data collector, and exothermic rising properties are judged in terms of the temperature after elapsing 3 minutes.

The heat generation test of the heat generating body follows the JIS temperature characteristic test.

In the iron powder or active iron powder in the oxidizing gas-treated heat generating composition, at least a part of the surface thereof is covered by an oxygen-containing film of iron. The degree of covering on the surface of the oxygen-containing film of iron is not limited so far as at least a part of the surface thereof is covered, and the surface may be entirely covered. In the case of the heat generating composition of the invention, since an ion of the reaction accelerator such as a chlorine ion is contained in the heat generating composition, there is no corrosion effect of the oxide film due to anti-corrosion effect by the ion of the reaction accelerator such as a chlorine ion. Thus, the oxidation reaction which is a sort of corrosion is not hindered. In particular, in the case where an oxygen-containing film of iron is prepared while the ion of the reaction accelerator such as a chlorine ion exists together, the subject effect is large. In the case where a metal other than iron is present on the surface, it is only required that at least other part of the metal portion other than iron is covered by the oxygen-containing film of iron.

In the iron powder of the invention, not only a region where (1) entire (uniform) corrosion, (2) pitting or crevice corrosion, (3) stress corrosion cracking, or the like is generated, but also irregularities or crevices are formed. For that reason, it is assumed that the iron powder of the invention has hydrophilicity and oxidation catalytic properties (FeO, etc.) in its own portion. In producing the heat generating composition, it is important that the iron powder has an oxygen-containing film in its own portion without relying upon mixing. In particular, in the iron component as prepared by contact treating the iron component and the reaction accelerator and water as essential components with an oxidizing gas, it is thought that a reaction active part composed mainly of an oxide, a hydroxide, a chlorine ion, a hydrogen ion, etc. is formed, whereby exothermic reactivity and hydrophilicity are improved and exothermic rising properties and moldability are remarkably improved.

With respect to (B), the amount of FeO (wustite) which is contained in the iron component containing a prescribed amount of wustite is usually from 2 to 50% by weight, preferably from 2 to 40% by weight, more preferably from 2 to 30% by weight, further preferably from 5 to 30% by weight, and still further preferably from 6 to 30% by weight in terms of an X-ray peak intensity ratio of iron. When the amount of FeO (wustite) exceeds 50% by weight, though the exothermic rising properties are good, the duration of heat generation becomes short. On the other hand, when it is less than 2% by weight, the exothermic rising properties become dull.

The thickness of the oxygen-containing film of a prescribed amount or the oxygen-containing film of iron powder containing wustite and the amount of wustite are applied to the heat generating composition or the heat generating composition molded body at the time of lamination.

An iron powder containing a carbon component and/or covered by a carbon component is also preferable. Although a proportion of the carbon component is not limited so far as a ratio of the iron component to the carbon component is 50% by weight or more, an iron powder in which the surface thereof is partially covered by from 0.3 to 3.0% by weight of a conductive carbonaceous substance is useful. Examples of the conductive carbonaceous substance include carbon black, active carbon, carbon nanotubes, carbon nanohorns, and flullerenes. Ones which have become conductive by doping are also employable. Examples of the iron powder include reduced iron powders, atomized iron powders, and sponge iron powders. In particular, the case where the conductive carbonaceous substance is active carbon and the iron powder is a reduced iron powder is useful as a heat generating body.

Furthermore, in order to efficiently carry out covering by a conductive carbonaceous substance, an oil such as a spindle oil may be added in an amount of from 0.01 to 0.05% by weight to such an extent that the fluidity of the iron powder is not hindered.

In the case of measuring the water mobility value of the heat generating composition in the heat generating body and the thickness and amount of wustite of the iron oxide film of iron powder in the mixture or the heat generating composition in the heat generating body, the heat generating composition or mixture may be measured according to the following items.

1) Water Mobility Value:

The heat generating composition is taken out from the heat generating body and measured according to the foregoing method of measuring a water mobility value.

2) Thickness and Amount of Wustite of Iron Oxide Film of Iron Powder:

A measuring sample as prepared by dispersing the heat generating composition, the heat generating composition molded body, the heat generating composition compression molded body or the mixture in nitrogen-purged ion-exchanged water in a nitrogen atmosphere, separating the iron powder using a magnet and drying the iron powder in a nitrogen atmosphere is used.

The heat generating composition of the invention contains, as essential components, an iron powder, a carbon component, a reaction accelerator and water, and its production process is one which can be put into practical use on an industrial scale. A reaction mixture containing, as essential components, an iron powder, a reaction accelerator and water and having a water content of from 1 to 20% by weight and a water mobility value showing a surplus water content of less than 0.01 is brought into contact with an oxidizing gas under circumstances at 0° C. or higher, a temperature rise of the reaction mixture is regulated at 1° C. or more within 10 minutes to produce a heat generating mixture, and the subject heat generating mixture is used as a raw material to form a heat generating composition. Alternatively, a heat generating composition may be formed by subsequently further adjusting the water content, or by further adding a carbon component, etc. and adjusting the water content.

In the invention, it has become possible to realize the contact treatment with an oxidizing gas within a short period of time by regulating the water content of the reaction mixture at a fixed amount or less, especially regulating the surplus water content of the reaction mixture at a fixed amount or less and carrying out an oxidizing contact treatment. By specifying the surplus water content and performing the treatment within a short period of time, adverse influences such as poor initial exothermic rising of the heat generating composition and shortening of the heat generation-retaining time can be avoided. Thus, it has become possible to establish an industrial mass-production process. Furthermore, although stirring or the like may not be achieved during the contact treatment with an oxidizing gas, when stirring or the like is achieved, the contact treatment with an oxidizing gas can be surely carried out.

Here, so far as the iron powder is partially oxidized, the state of the reaction mixture or heat generating mixture at the time of the contact treatment with an oxidizing gas may be any of a standing state, a transfer state, or a fluidizing state by stirring, etc. and may be properly selected. Furthermore, the circumstances at the time of mixing the respective components of the reaction mixture, the heat generating mixture or the heat generating composition and at the time of mixing at the time of adjusting the water content are not limited, and examples thereof include those in an oxidizing gas atmosphere and those in blowing of an oxidizing gas.

The "adjustment of the water content" as referred to herein means that after contact treating the heat generating mixture with an oxidizing gas, water or an aqueous solution of a reaction accelerator is added. Although the amount of addition of water or an aqueous solution of a reaction accelerator is not limited, examples thereof include the addition of a weight corresponding to a reduced weight by the contact treatment and the addition of a weight such that a desired water mobility value is obtained.

Whether or nor the adjustment of the water content is introduced may be properly determined depending upon the utility.

The heat generating composition of the invention contains, as essential components, an iron powder, a carbon component, a reaction accelerator and water and is started from a mixture obtained by contact treating a reaction mixture containing, as essential components, an iron powder, a reaction accelerator and water with an oxidizing gas. The heat generating composition of the invention is usually one obtained by adjusting the water content of a heat generating mixture and is a heat generating composition which is satisfactory in the exothermic rising, has a suitable amount of surplus water and has excellent moldability. Furthermore, it is possible to produce a heat generating body which can become promptly warm at the time of use.

Accordingly, at least the iron powder further including the carbon component has a history of oxidation by the contact treatment with an oxidizing gas, and it is thought that this is deeply related to excellent exothermic rising properties, exothermic endurance and excellent moldability.

When the iron powder which is contact treated with an oxidizing gas according to the invention is used, the amount of addition of the carbon component (for example, active carbon) in the heat generating composition can be reduced by, for example, 20% or more. By reducing the amount of addition of the carbon component, the costs are lowered.

According to the production process of the heat generating mixture of the invention, it is possible to obtain a heat generating composition having excellent exothermic rising properties, excellent hydrophilicity, and excellent moldability. In particular, a heat generating composition having remarkably excellent moldability and exothermic characteristics together can be obtained while specifying the water availability value at from 0.01 to 50, in particular from 0.01 to 20.

The heat generating composition as produced by the production process of the invention is remarkably improved with respect to exothermic rising properties. Thus, the amount of addition of the carbon component (such as active carbon) in the heat generating composition can be reduced by, for example, 20% or more so that it can contribute to a reduction in costs.

Furthermore, since the hydrophilicity is remarkably improved, the moldability with a mold is remarkably improved. Thus, since after molding, collapsed pieces of the heat generating composition are not scattered on the surroundings of the heat generating composition molded body, sealing can be appropriately achieved so that a heat generating body free from sealing cut can be produced. In this way, heat generating composition molded bodies of various shapes can be produced, and heat generating bodies of various shapes are formed.

Furthermore, in view of improving the exothermic rising properties of the heat generating composition, the following are preferable.

1) A heat generating composition obtained by a contact treatment (self heat generation) of a mixture of the essential components of the heat generating composition, or a mixture of the foregoing mixture and an acidic substance or other necessary components with an oxidizing gas, a heat generating composition obtained by additionally adjusting the water content of the foregoing heat generating composition, or a heat generating composition obtained by adding and mixing other components in the foregoing heat generating composition.

2) Any one of the following active iron powders having an oxygen-containing film (for example, oxides) on at least a part of the surface thereof is used as the iron powder: (a) an iron powder having an oxygen-containing film of iron having a thickness, as measured by the Auger electron spectroscopy, of 3 nm or more on the surface thereof and (b) an iron powder having a content of wustite of from 2 to 50% by weight in terms of an X-ray peak intensity ratio to iron.

3) A mixture of an active iron powder having an oxygen-containing film (for example, oxides) on at least a part of the surface thereof and an iron powder not having an oxygen-containing film is used as the iron powder. In this case, a mixture containing 60% by weight or more of an active iron powder and less than 40% by weight of an iron powder other than the active iron is preferable.

In the case of storing the heat generating composition which is treated with an oxidizing gas or the heat generating composition containing an active iron powder, or a material utilizing the same over a long period of time, it is preferred to combine a hydrogen formation inhibitor therewith. This is because in this way, a heat generating body having excellent exothermic characteristics, which is inhibited in the formation of hydrogen, is free from swelling of the outer bag at the time of storage, etc. and has satisfactory exothermic rising properties, is obtained.

Furthermore, so far as the rising characteristics are not affected, the heat generating composition having a water mobility value falling outside the range of from 0.01 to 20 can contain a water-soluble polymer, a flocculant aid, a flocculant, an agglomeration aid, a dry binding material, a dry binding agent, a dry binder, an adhesive raw material, a tackifier, an excipient, a flocculating agent, or a soluble sticky raw material.

Furthermore, since a marketed heat generating body in which a heat generating composition is accommodated in an accommodating bag is provided on the assumption that it is accommodated in an outer bag which is an air-impermeable accommodating bag and is storable over a long period of time, it is preferred to use a heat generating composition containing a hydrogen formation inhibitor. Since the heat generating composition which has passed through the contact treatment with an oxidizing gas is an active composition, it is important that the heat generating composition contains a hydrogen formation inhibitor. Also, this efficacy is further strengthened by using a pH adjusting agent together.

Furthermore, so far as the reaction characteristics and exothermic characteristics are not affected, the heat generating composition having a water mobility value of less than 0.01 may contain a flocculant aid, a flocculant, an agglomeration aid, a dry binder, a dry binding agent, a dry binding material, a sticky raw material, a thickener, an excipient, or a water-soluble polymer in an amount ranging from 0.01 to 3 parts by weight respectively.

The "flocculent aid" as referred to herein is a flocculant aid as described in Japanese Patent No. 3,161,605 (JP-T-11-508314) such as gelatin, natural gum, and corn syrup.

The "flocculant" as referred to herein is a flocculant as described in JP-T-2002-514104 such as corn syrup and maltitol syrup.

The "agglomeration aid" as referred to herein is an agglomeration aid as described in JP-T-2001-507593 such as corn syrup.

The "dry binder" as referred to herein is a dry binder as described in JP-T-2002-514104 such as microcrystalline cellulose, maltodextrin, and mixtures thereof.

The "dry binding agent" as referred to herein is a dry binding agent as described in JP-T-2001-507593 such as maltodextrin and sprayed lactose.

The "dry binding material" as referred to herein is a dry binding material as described in JP-T-11-508314 such as microcrystalline cellulose, maltodextrin, and mixtures thereof.

The "sticky raw material" or the "binder" as referred to herein is a sticky raw material or binder as described in JP-A-4-293989 such as water glass, polyvinyl alcohol (PVA), and carboxymethyl cellulose (CMC).

The "thickener" as referred to herein is a thickener as described in JP-A-6-343658 such as corn starch and potato starch.

The "excipient" as referred to herein is an excipient as described in JP-A-7-194641 such as α-starch and sodium alginate.

As the "water-soluble polymer" as referred to herein, the water-soluble polymer in the adhesive layer can be used.

The particle size of the water-insoluble solid component constituting the moldable heat generating composition of the invention is not limited so far as the heat generating composition has moldability. In the case where any one of length, width and height as the size of the heat generating composition molded body as molded from the heat generating composition is small, the moldability is improved by making the particle size small.

In addition, it is preferable in view of molding that the particle size of the solid component constituting the moldable heat generating composition is small. A maximum particle size of the water-insoluble solid component exclusive of the reaction accelerator and water in the components constituting the moldable heat generating composition is preferably not more than 2.5 mm, more preferably not more than 930 μm, further preferably not more than 500 μm, still further preferably not more than 300 μm, even further preferably not more than 250 μm, and even still further preferably not more than 200 μm. Moreover, 80% or more of the particle size of the solid component is usually not more than 500 μm, preferably not more than 300 μm, more preferably not more than 250 μm, further preferably not more than 200 μm, still further preferably not more than 150 μm, and even further preferably not more than 100 μm.

Incidentally, with respect to the particle size of the water-insoluble solid component, separation is conducted using a sieve, and the particle size of the component which has passed through the sieve is calculated from an opening of the sieve. That is, sieves of 8, 12, 20, 32, 42, 60, 80, 100, 115, 150, 200, 250 and 280 meshes and a receiving dish are combined in this order from up to down. About 50 g of water-insoluble solid component particles are placed on the uppermost 8-mesh sieve and shaken for one minute using an automatic shaker. Weights of the water-insoluble solid component particles on each of the sieves and the receiving dish are weighed. The total amount thereof is defined as 100%, and the particle size distribution is determined from weight fractions. When the sum of all receiving dishes under the sieve of a specific mesh size becomes 100% which is the total sum of the particle size distribution, the size (μm) calculated from the opening of the specific mesh is defined as the particle size of the water-insoluble solid component.

Incidentally, each of the mesh sieves may be combined with other mesh sieves. Here, the particles which have passed through a 16-mesh sieve are defined to have a particle size of not more than 1 mm; the particles which have passed through a 20-mesh sieve are defined to have a particle size of not more than 850 μm; the particles which have passed through a 48-mesh sieve are defined to have a particle size of not more than 300 μm; the particles which have passed through a 60-mesh sieve are defined to have a particle size of not more than 250 μm; the particles which have passed through a 65-mesh sieve are defined to have a particle size of not more than 200 μm; the particles which have passed through an 80-mesh sieve are defined to have a particle size of not more than 180 μm; the particles which have passed through a 100-mesh sieve are defined to have a particle size of not more than 150 μm; the particles which have passed through a 115-mesh sieve are defined to have a particle size of not more than 120 μm; the particles which have passed through a 150-mesh sieve are defined to have a particle size of not more than 100 μm; and the particles which have passed through a 250-mesh sieve are defined to have a particle size of not more 63 μm, respectively. The same is applicable to mesh sizes of less than these mesh sizes.

Furthermore, the heat generating composition can be classified into a powder, a granulate heat generating composition (having a water mobility value of less than 0.01) a moldable heat generating composition (having a water mobility value of from 0.01 to 20), and a sherbet-like heat generating composition (having a water mobility value exceeding 20 but not more than 50) depending upon the state of adjustment of the water content or surplus water. The heat generating composition as classified depending upon the water mobility value is as described previously.

The "moldability" as referred to in the invention exhibits that a laminate of the heat generating composition having a cavity or concave die shape can be formed by force-through molding using a trimming die having a cavity or cast molding using a concave die and after molding including mold release, the molding shape of the heat generating composition molded body is held. When the moldability is revealed, since the shape is held until the heat generating composition molded article is at least covered by a covering material and a seal part is formed between the substrate and the covering material, sealing can be achieved in the periphery of the shape with a desired shape. Also, since so-called "spots" which are a collapsed piece of the heat generating composition are not scattered in the seal part, sealing can be achieved without causing cutting in seal. The presence of the spots causes insufficient sealing.

Next, with respect to the moldability, a measurement device, a measurement method and a judgment method will be described below.

1) Measurement Device:

With respect to the measurement device, a stainless steel-made molding die (a plate having a size of 2 mm in thickness×200 mm in length×200 mm in width and having a cavity as treated by R5 in four corners of 60 mm in length×40 mm in width in a central part thereof) and a fixable leveling plate are disposed above a travelable endless belt, and magnets (two magnets having a size of 12.5 mm in thickness×24 mm in length×24 mm in width are disposed in parallel) are disposed under the endless belt. The magnets should cover a region of the leveling plate and the vicinity thereof and a region larger than a region covered by a cut side (40 mm) vertical to the advancing direction of the cavity of the molding die.

2) Measurement Method:

With respect to the measurement method, a stainless steel plate having a size of 1 mm in thickness×200 mm in length×200 mm in width is placed on the endless belt of the measurement device, a polyethylene film having a size of 70 μm in thickness×200 mm in length×200 mm in width is placed thereon, and a stainless steel-made molding die is further placed thereon. Thereafter, a leveling plate is fixed in a position of the cavity of the molding die of 50 mm far from the end portion in the advancing direction of the endless belt, 50 g of a heat generating composition is then placed in the vicinity of the leveling plate between the leveling plate and the cavity, and the heat generating composition is filled in the cavity of the molding die while leveling it by moving the endless belt at 1.8 m/min.

After the molding die has completely passed through the leveling plate, the traveling of the endless belt is stopped. Next, the molding die is removed, and a heat generating composition molded body as laminated on the polyethylene film is observed.

3) Judgment Method:

With respect to the judgment method, in the surroundings of the heat generating composition molded body, in the case where any collapsed piece of the heat generating composition molded body exceeding a maximum length of 800 μm is not present and the number of collapsed pieces of the heat generating composition molded body having a maximum length of from 300 to 800 μm is not more than 5, it is to be noted that the heat generating composition has moldability. The moldability is an essential property for a heat generating composition to be used in the molding system. If the heat generating composition does not have moldability, it is impossible to produce a heat generating body by the molding system.

The heat generating composition of the invention has resistance to compression. The "resistance to compression" as referred to herein means that a heat generating composition compressed body obtained by compressing a heat generating composition molded body as accommodated in a molding die within the die to such an extent that the thickness is 70% of the die thickness holds 80% or more of exothermic rising properties of the exothermic rising properties of the heat generating composition molded body before compression (a difference in temperature between one minute and 3 minutes after starting a heat generation test of the heat generating composition).

Here, the measurement method of exothermic rinsing properties for the resistance to compression will be described below.

1. Heat Generating Composition Molded Body:

1) A magnet is provided in the vicinity of a central part of the back side of a polyvinyl chloride-made supporting plate (5 mm in thickness×600 mm in length×600 mm in width) of a footed supporting table so as to cover a cavity shape of a molding die.

2) A temperature sensor is placed on the central part the surface of the supporting plate.

3) A polyethylene film (25 μm in thickness×250 mm in length×200 mm in width) as provided with an adhesive layer having a thickness of about 80 μm is stuck onto the supporting plate via a sticky layer such that the center of the polyethylene film is positioned at the sensor.

4) On an underlay plate (280 mm in length×150 mm in width×50 μm to 2 mm in thickness), a polyethylene film (230 mm in length×155 mm in width×25 μm to 100 μm in thickness) is placed such that one end of the polyethylene film is projected by about 20 mm outside the underlay plate and that one end thereof in the length direction is substantially coincident with one end of the underlay plate.

5) A template (230 mm in length×120 mm in width×3 mm in thickness) having a cavity (80 mm in length×50 mm in width×3 mm in height) is placed on the polyethylen film placed on the underlay plate; a template is placed on the polyethylene film such that one end thereof in the length direction is fitted to one end where the underlay plate and the polyethylene film are coincident with each other and that in the width direction, one end part of the width of the template is placed at a position of the central part by about 20 mm far from an opposing end to the side where the polyethylene film is projected outward from the underlay plate. Next, the resulting assembly is placed on the supporting plate together with the underlay plate.

6) A sample is placed in the vicinity of the cavity; a force-in die plate is moved along the molding die; the sample is charged into the cavity while stuffing; and the sample is leveled while stuffing along the template plane (force-in die molding), thereby filling the sample in the die.

7) Next, the magnet beneath the supporting plate is removed; the end portion of the projected polyethylene film is pressed; the underlay plate is removed; and the temperature measurement is started.

2. Heat Generating Composition Compressed Body:

1) to 6) are the same as in the case of the heat generating composition molded body.

8) A die having a convex having a thickness of 0.9 mm which can substantially tightly come into the cavity in relation of the cavity with an unevenness is fitted to the cavity and compressed by a roll press or plate press to prepare a heat generating composition compressed body having a thickness of 2.1 mm (compressed to 70% of the die thickness) within the die.

9) The resulting assembly is placed on the supporting plate together with the underlay plate; the magnet beneath the supporting plate is removed; the end portion of the projected polyethylene film is pressed; the underlay plate is removed; and the temperature measurement is started.

With respect to the measurement of the exothermic temperature, the temperature is measured for 5 minutes at a measurement timing of 2 seconds using a data collector, and resistance to compression is judged in terms of a difference in temperature between after elapsing one minute and after elapsing 3 minutes.

The thickness after compression is preferably from 50 to 99.5%, more preferably from 60 to 99.5%, and further preferably from 60 to 95% of the die thickness.

Incidentally, in the invention, it is to be noted that the heat generating composition molded body includes a heat generating composition compressed body.

Furthermore, at least one of the thicknesses of the heat generating composition molded bodies in the sectional exothermic parts may be different.

By making the thickness of each of the heat generating composition molded bodies different, it is possible to make the temperature characteristics of the heat generating composition molded body such as exothermic time, exothermic rising properties, and exothermic peak temperature different. Thus, in a heat generating body having sectional exothermic parts, by providing sectional exothermic parts in which heat generating composition molded bodies having a different thickness are properly disposed, sectional exothermic parts having different temperature characteristics such as exothermic time, exothermic rising properties, and exothermic peak temperature exist, thereby deviating the exothermic time, the exothermic rising properties and the exothermic peak temperature among the sectional exothermic parts. There is thus obtained a heat generating body having desired temperature distribution, exothermic time, exothermic rising properties and exothermic peak temperature. A method for making the thickness of each of the heat generating composition molded bodies different is not limited. Examples thereof include a method in which the heat generating composition molded bodies are compressed so as to have a different degree of compression by using a compressor with pushing parts having a different height, thereby making the thickness of each of the heat generating molded bodies different; and a method in which the heat generating composition molded bodies are compressed so as to have a different degree of compression by using rubber rolls having a different surface elasticity, thereby making the thickness of each of the heat generating molded bodies different.

Further, the shape of the heat generating body may be any shape. A shape selected from the group consisting of a rectangular shape, a circular shape, an elliptical shape, a polygonal shape, a broad bean-like shape, an eye mask-like shape, a cocoon-like shape, a gourd-like shape, a rectangular shape with rounded corners, a square shape with rounded corners, an egg-like shape, a boomerang-like shape, a comma-shaped bead-like shape, a wing-like shape, a nose-like shape, a star-like shape, and a foot-like shape can be used.

Furthermore, as other example of the heat generating body of the invention, a pocket heat generating body having specified physical dimensions and filling characteristic, capable of continuously causing heat generation over a long period of time and giving improved temperature control properties may be formed by incorporating the heat generating composition molded body into a pocket of a substrate having a pocket. This pocket heat generating body contains a heat generating composition molded body based on a specified oxidation chemical reaction of iron, and this heat generating composition molded body fills an effective capacity of the pocket within the pocket heat generating body, thereby reducing a surplus spacial capacity which may be possibly present and minimizing an ability of the heat generating composition molded body or the heat generating substance to move within the sectional exothermic part. Since such a pocket heat generating body has flexible physical dimensions, it can be easily incorporated into a body worn implement which is able to adapt to an external form of every body and can constantly achieve warming of the body conveniently and comfortably, and the like.

Examples thereof include heat cells and all heat generating bodies using the same as described in JP-T-11-508786, JP-T-11-508314, JP-T-11-512954, JP-T-2002-514104, JP-T-2003-509120, JP-T-2001-5075930, and so on, which are useful in the invention and the disclosures of which are incorporated in this description by reference.

In this case, in the case where two or more plural pockets are provided at intervals, a perforation may be provided in at least one pocket.

Furthermore, at least one of the thicknesses of the pockets in the sectional exothermic parts may be different.

By making the thickness of each of the heat generating composition molded bodies different, it is possible to make the temperature characteristics of the heat generating composition molded body such as exothermic time, exothermic rising properties, and exothermic peak temperature different. Thus, in the heat generating body having a pocket, by providing pockets in which heat generating composition molded bodies having a different thickness are properly disposed, sectional exothermic parts having different temperature characteristics such as exothermic time, exothermic rising properties, and exothermic peak temperature exist, thereby deviating the exothermic time, the exothermic rising properties and the exothermic peak temperature among the pockets. There is thus obtained a heat generating body having desired temperature distribution, exothermic time, exothermic rising properties and exothermic peak temperature. A method for making the thickness of each of the heat generating composition molded bodies different is not limited. Examples thereof include a method in which the heat generating composition molded bodies are compressed so as to have a different degree of compression by using a compressor with pushing parts having a different height, thereby making the thickness of each of the heat generating molded bodies different; and a method in which the heat generating composition molded bodies are compressed so as to have a different degree of compression by using rubber rolls having a different surface elasticity, thereby making the thickness of each of the heat generating molded bodies different.

The fixing means is not limited so far as it has capability for fixing a thermal packaging body for joint surroundings or a material having an exothermic part to a prescribed part.

As the fixing means, an adhesive layer, a hook and eye, a hook and button, a hook and loop fastener such as Velcro, a magnet, a band, a string, and combination thereof can be arbitrarily used.

Incidentally, in the case of a band, fixing means for adjustment may be further constructed by a combination of a hook and loop fastener and an adhesive layer.

Here, the "hook and loop fastener" as referred to herein has a fastening function by a combination of a loop as a female fastener with a male fastener capable of fastening the female fastener thereto, which is known as trade names such as Magic Tape (a registered trademark), Magic Fastener (a registered trademark), Velcro Fastener, and Hook and Loop Tape. Examples of the material having a loop function include non-woven fabrics and woven fabrics of napped or hole-containing yarns. Such a material having a loop function (female fastener function) may be covered on the surface of a paddling forming the band, or the band may be constructed of such a material itself. Although the hook member which is the male fastener member is not particularly limited, examples thereof include hook members formed of a polyolefin based resin (for example, polyethylene and polypropylene), a polyamide, a polyester, etc. Although the shape of the hook is not particularly limited, a hook having a cross-sectional shape such as an I type, an inverted L type, an inverted J type, and a so-called mushroom type is preferable because it is easily hooked by the loop and does not give an extreme stimulus to the skin. Incidentally, the hook may be adhered to the entire area of a fastening tape, and only the hook may be used as a fastening tape while omitting a tape substrate.

The adhesive layer may contain at least one member selected from additional components consisting of a water retaining agent, a water absorptive polymer, a pH adjusting agent, a surfactant, an organosilicon compound, a hydrophobic polymer compound, a pyroelectric substance, an antioxidant, an aggregate, a fibrous material, a moisturizer, a functional substance, and a mixture thereof.

The adhesive of the invention is classified into a non-hydrophilic adhesive, a mixed adhesive, and a hydrophilic adhesive (for example, a gel).

The adhesive constituting the adhesive layer is not limited so far as it has an adhesive strength necessary for adhering to the skin or clothes. Adhesives of every form such as a solvent based adhesive, an aqueous adhesive, an emulsion type adhesive, a hot melt type adhesive, a reactive adhesive, a pressure-sensitive adhesive, a non-hydrophilic adhesive, and a hydrophilic adhesive are employable.

The adhesive layer includes one layer of a non-hydrophilic adhesive constituted of the non-hydrophilic adhesive and non-hydrophilic adhesive layers constituted of the non-hydrophilic adhesive.

It is to be noted that a material whose water absorption properties are improving by containing a water absorptive polymer or a water retaining agent in the non-hydrophilic adhesive layer is dealt as the non-hydrophilic adhesive layer.

A hot melt based adhesive may be provided between the hydrophilic adhesive layer and a substrate or a covering material.

Furthermore, in the case where the hydrophilic adhesive is provided in a thermal packaging body for joint surroundings, there is no limitation. After seal treating a thermal packaging body for joint surroundings, a hydrophilic adhesive layer may be provided in the thermal packaging body for joint surroundings.

Furthermore, the adhesive layer may or may not have air permeability and may be properly selected depending upon the utility. With respect to the air permeability, the adhesive layer may be air-permeable as a whole. Examples thereof include an adhesive layer having air permeability as a whole of a region in which an adhesive is partially present and a portion where no adhesive is present is partially present.

In laminating an adhesive on an air-permeable substrate and/or a covering material in a stratiform state as it is, examples of a method for keeping its air permeability include a method in which an adhesive layer is partially laminated by printing or transferring an adhesive, thereby forming a non-laminated part as an air-permeable part; a method in which an adhesive is transferred in one direction while drawing a circle in a filament-like form or properly moved in the two-dimensional directions by transferring in a zigzag manner, whereby a space of the filament-like adhesive keeps air permeability or moisture permeability or the adhesive is foamed; and a method for forming a layer by a melt blow system.

Examples of the adhesive which constitutes the non-hydrophilic adhesive layer include acrylic adhesives, polyvinyl acetate based adhesives (for example, vinyl acetate resin based emulsions and ethylene-vinyl acetate resin based holt melt adhesives), polyvinyl alcohol based adhesives, polyvinyl acetal based adhesives, vinyl chloride based adhesives, polyamide based adhesives, polyethylene based adhesives, cellulose based adhesives, chloroprene (neoprene) based adhesives, nitrile rubber based adhesives, polysulfide based adhesives, butyl rubber based adhesives, silicone rubber based adhesives, styrene based adhesives (for example, styrene based hot melt adhesives), rubber based adhesives, and silicone based adhesives. Of these, rubber based adhesives, acrylic adhesives, and adhesives containing a hot melt based polymer substance for the reasons that they are high in the adhesive strength, are cheap, are good in long-term stability, and are small in reduction of the adhesive strength even by providing heat.

In addition to the base polymer, if desired, the adhesive may be compounded with other components such as tackifiers (for example, petroleum resins represented by rosins, chroman-indene resins, hydrogenated petroleum resins, maleic anhydride-modified rosins, rosin derivatives, and C-5 based petroleum resins), phenol based tackifiers (especially, tackifiers having an aniline point of not higher than 50° C.; for example, terpene phenol based resins, rosin phenol based resins, and alkylphenol based resins), softeners (for example, coconut oil, castor oil, olive oil, camellia oil, and liquid paraffin), softeners, anti-aging agents, fillers, aggregates, adhesion adjusting agents, adhesion modifiers, coloring agents, anti-foaming agents, thickeners, and modifiers, thereby improving performance such as an improvement in adhesion to nylon-made clothes and mixed yarn clothes.

Examples of the hot melt based adhesive include known hot melt based adhesives imparted with adhesion. Specific examples thereof include styrene based adhesives made of, as a base polymer, an A-B-A type block copolymer (for example, SIS, SBS, SEBS, and SIPS), vinyl chloride based adhesives made of, as a base polymer, a vinyl chloride resin, polyester based adhesives made of, as a base polymer, a polyester, polyamide based adhesives made of, as a base polymer, a polyamide, acrylic adhesives made of, as a base polymer, an acrylic resin, polyolefin based adhesives made of, as a base polymer, a polyolefin (for example, polyethylene, super low density polyethylene, polypropylene, ethylene-α-olefin copolymers, and ethylene-vinyl acetate copolymers), 1,2-polybutadiene based adhesives made of, as a base polymer, 1,2-polybutadiene, and polyurethane based adhesives made of, as a base polymer, polyurethane; adhesives made of a modified body of the foregoing adhesive whose adhesion is improved or whose stability is changed; and mixtures of two or more kinds of these adhesives. Adhesive layers constituted of a foamed adhesive and adhesive layers constituted of a crosslinked adhesive can also be employed.

The non-aromatic hot melt based adhesive is not limited so far as it is made of, as a base polymer, a hot melt based adhesive not containing an aromatic ring. Examples thereof include olefin based hot melt based adhesives and acrylic hot melt based adhesives. As the non-aromatic polymer which is the base polymer not containing an aromatic ring, there are enumerated polymers or copolymers of an olefin or a diene. Examples thereof include olefin polymers. The olefin polymer includes polymers or copolymers of ethylene or an α-olefin. Also, polymers resulting from adding a diene (for example, butadiene and isoprene) as other monomer thereto may be employed.

The α-olefin is not limited so far as it is a monomer having a double bond in the terminal thereof. Examples thereof include propylene, butene, heptane, hexene, and octene.

The "aromatic hot melt based adhesive" as referred to herein is a hot melt based adhesive whose base polymer contains an aromatic ring. Examples thereof include styrene based hot melt based adhesives represented by A-B-A type block copolymers.

In the foregoing A-B-A type block copolymers, the A block is a non-elastic polymer block made of a monovinyl substituted aromatic compound A such as styrene and methylstyrene; and the B block is an elastic polymer block made of a conjugated diene such as butadiene and isoprene. Specific examples thereof include a styrene-butadiene-styrene block copolymer (SBS), a styrene-isoprene-styrene block copolymer (SIS), and hydrogenated types thereof (for example, SEBS and SIPS), and mixtures thereof.

As a countermeasure for preventing a lowering of adhesive strength caused due to an increase of water of the non-hydrophilic adhesive layer, an adhesive layer obtained by further compounding a water absorptive polymer in the non-hydrophilic adhesive can be used.

The hydrophilic adhesive which constitutes the hydrophilic adhesive layer is not particularly limited so far as it contains a hydrophilic polymer or a water-soluble polymer as the major component, has adhesion and is hydrophilic as an adhesive.

Examples of the constitutional components of the hydrophilic adhesive include hydrophilic polymers (for example, polyacrylic acid), water-soluble polymers (for example, poly(sodium acrylate) and polyvinylpyrrolidone), crosslinking agents (for example, dry aluminum hydroxide and meta-silicic acid aluminic acid metal salts), softeners (for example, glycerin and propylene glycol), higher hydrocarbons (for example, soft liquid paraffin and polybutene), primary alcohol fatty acid esters (for example, isopropyl myristate), silicon-containing compounds (for example, silicone oil), fatty acid glycerin esters (for example monoglycerides), oily components (for example, vegetable oils such as olive oil), antiseptics (for example, methyl p-hydroxybenzoate and propyl p-hydroxybenzoate), solubilizing agents (for example, N-methyl-2-pyrrolidone), thickeners (for example, carboxymethyl cellulose), surfactants (for example, polyoxyethylene hardened castor oil and sorbitan fatty acid esters), hydroxycarboxylic acid (for example, tartaric acid), excipients (for example, light silicic anhydride, water absorptive polymers, and kaolin), moisturizers (for example, D-sorbitol), stabilizers (for example, sodium edetate, p-hydroxybenzoic acid esters, and tartaric acid), crosslinking type water absorptive polymers, boron compounds (for example, boric acid), and water. They may be used as an arbitrary combination.

A temporary adhering seal part is formed via a sticky layer. An adhesive which constitutes the sticky layer is a layer formed of a polymer composition which is tacky at the normal temperature and is not limited so far as it can be heat sealed after temporary adhesion.

Furthermore, the foregoing adhesives of the sticky layer can be used as the adhesive which constitutes the sticky layer as used for temporary adhesion. Of these, non-hydrophilic adhesives are preferable. With respect to the adhesive constituting the adhesive layer, it is preferable that the adhesive is well compatible with a heat seal material constituting a heat seal and that a melting point of the base polymer of, the adhesive is not higher than a melting point of the heat seal material. Hot melt based adhesives are especially preferable for hot melt based bonding agents. Furthermore, in the case where the heat seal material is an olefin based raw material, preferred examples thereof include olefin based adhesives.

A bonding layer for fixing the air permeability adjusting material is constituted of a bonding agent or an adhesive which is usually used. In particular, an adhesive is useful, and the foregoing adhesives for constituting the adhesive layer can be used.

Furthermore, a method for providing a bonding layer is not limited so far as the air permeability adjusting material can be fixed. The bonding layer may be entirely provided or partially or intermittently provided. Examples of its shape include various shapes such as a network-like shape, a stripe-like shape, a dot-like shape, and strip-like shape.

Furthermore, in the case where an adhesive layer is employed as the hydrophilic adhesive layer, if there is a difference in a water retaining force between the hydrophilic adhesive layer and the heat generating composition molded body, transfer of water occurs via a packaging material present therebetween such as a substrate, thereby causing in-conveniences against the both. In particular, the transfer of water occurs during the storage. In order to prevent this, it is preferable that the packaging material present therebetween at least has a moisture permeability of not more than 2 $g/m^2/$day in terms of a moisture permeability according to the Lyssy method. By using this, in the case where the heat generating body is accommodated in an outer bag as an air-impermeable accommodating bag and stored, the transfer of water can be prevented.

In the case where a hydrophilic adhesive layer is used as the adhesive layer, the moisture permeability of a moisture-proof packaging material provided between the heat generating composition molded body and the hydrophilic adhesive layer is not limited so far as the transfer of water can be prevented within the range where the exothermic performance is not affected. The moisture permeability according to the Lyssy method is usually not more than 2 $g/m^2/$day, preferably not more than 1.0 $g/m^2/$day, more preferably not more than 0.5 $g/m^2/$day, and further preferably from 0.01 to 0.5 $g/m^2/$day. These values are a value under a condition under an atmospheric pressure at 40° C. and 90% RH. Incidentally, the moisture-proof packaging material can be used as a substrate or a covering material and may be laminated singly on a substrate, a covering material, or the like.

The moisture-proof packaging material is not limited so far as the transfer of water between the heat generating composition molded body and the hydrophilic adhesive layer can be prevented. Examples thereof include metal vapor deposited films, vapor deposited films of a metal oxide, metal foil-laminated films, EVOH (ethylene/vinyl alcohol copolymer or ethylene/vinyl acetate copolymer saponified product) based films, biaxially stretched polyvinyl alcohol films, polyvinylidene chloride coated films, polyvinylidene chloride coated films obtained by coating polyvinylidene chloride on a substrate film (for example, polypropylene), metal foils such as an aluminum foil, air-impermeable packaging materials obtained by vapor depositing or sputtering a metal (for example, aluminum) on a polyester film substrate, and packaging laminates using a transparent barrier film of a structure in which silicon oxide or aluminum oxide is provided on a flexible plastic substrate. The air-impermeable packaging materials which are used in the outer bag, etc. can also be used.

Furthermore, packaging materials such as moisture-proof packaging materials as described in JP-A-2002-200108, the disclosures of which can be incorporated herein by reference, can be used.

In the case of using a water-containing hydrophilic adhesive (for example, a gel) in the adhesive layer, in order to adjust the moisture equilibrium between the heat generating composition and the adhesive layer, the content of a reaction accelerator (for example, sodium chloride) or a substance having a water holding power (for example, a water absorptive polymer) in the heat generating composition may be adjusted within the range of from 10 to 40% by weight, preferably from 15 to 40% by weight, and more preferably from 15 to 30% by weight based on the heat generating composition.

Furthermore, as the adhesive having good moisture permeability and low stimulation to the skin, water-containing adhesives (for example, hydrophilic adhesives and gels) as described in JP-A-10-265373 and JP-A-9-87173, adhesives which can be subjected to hot melt coating as described in JP-A-6-145050 and JP-A-6-199660, and rubber based adhesives as described JP-A-10-279466 and JP-A-10-182408, the disclosures of which are totally incorporated herein by reference, are useful.

The functional substance which is contained in the adhesive layer is not limited so far as it is a substance having any function. There can be enumerated at least one member selected from aromatic compounds, vegetable extracts, crude drugs, perfumes, slimming agents, analgesics, blood circulation promoters, swelling improvers, antibacterial agents, sterilizers, mold inhibitors, odor eaters, deodorants, percutaneously absorptive drugs, fat-splitting components, minus ion generators, far infrared ray radiants, magnetic bodies, fomentations, cosmetics, bamboo vinegar, and wood vinegar.

Specific examples thereof include aromatic compounds (for example, menthol and benzaldehyde), vegetable extracts (for example, mugwort extract), crude drugs (for example, moxa), perfumes (for example, lavender and rosemary), slimming agents (for example, aminophylline and tea extract), analgesic drugs (for example, indomethacin and dl-camphor), blood circulation promoters (for example, acidic mucopolysaccharide and chamomile), swelling improvers (for example, horse chestnut extract and flavone derivatives), fomentations (for example, aqueous boric acid, physiological saline, and aqueous alcohols), fat-splitting components (for example, jujube extract, caffeine, and tonalin), cosmetics (for example, aloe extracts, vitamin preparations, hormone preparations, anti-histamines, and amino acids), antibacterial agents and sterilizers (for example, carbolic acid derivatives, boric acid, iodine preparations, invert soaps, salicylic acid based substances, sulfur, and antibiotics), and mold inhibitors.

The percutaneously absorptive drug is not particularly limited so far as it has percutaneous absorption. Examples thereof include corticosteroids, anti-inflammatory drugs, hypertension drugs, anesthetics, hypnotic sedatives, tranquilizers, antibacterial substances, antifungal substances, skin stimulants, inflammation inhibitors, anti-epileptics, analgesics, antipyretics, anesthetics, mold inhibitors, antimicrobial antibiotics, vitamins, antiviral agents, swelling improvers, diuretics, antihypertensives, coronary vasodilators, anti-tussive expectorants, slimming agents, anti-histamines, antiarrhythmic agents, cardiotonics, adrenocortical hormones, blood circulation promoters, local anesthetics, fat-splitting components, and mixtures thereof. However, it should not be construed that the invention is limited thereto. These drugs are used singly or in admixture of two or more kinds thereof as the need arises.

The content of such a functional substance is not particularly limited so far as it falls within the range where the effect of a medicine can be expected. However, from the viewpoints of adhesive strength as well as pharmacological effect and economy, the content of the functional substance is preferably from 0.01 to 25 parts by weight, and more preferably from 0.5 to 15 parts by weight based on 100 parts by weight of the adhesive.

Furthermore, a method for providing the adhesive layer is not limited so far as a thermal packaging body for joint surroundings can be fixed. The adhesive layer may be entirely provided or partially or intermittently provided. Examples of its shape include various shapes such as a network-like shape, a stripe-like shape, a dot-like shape, and strip-like shape.

The term "substantially planar" as referred to in the invention means a planar surface not having an accommodating concave such as an accommodating pocket, an accommodating section, and an accommodating zone as provided in advance for the purpose of accommodating the heat generating composition. Accordingly, irregularities which do not intentionally accommodate the heat generating composition may be present.

The "pocket" as referred to in the invention is an accommodating pocket which is provided in advance for the purpose of accommodating the heat generating composition and is a pocket as described in JP-T-2001-507593. Since irregularities which are not used for intentionally accommodating the heat generating composition molded body are not the pocket, even when such irregularities are present on a substrate, it is to be noted that such a substrate is defined as a substantially planar substrate.

The "accommodating section" as referred to herein is an accommodating section for accommodation as provided in advance on the packaging material for the purpose of accommodating the heat generating composition and is an accommodating section as described in Japanese Patent No. 3,161,605 and JP-T-11-508314. Since irregularities which are not used for intentionally accommodating the heat generating composition molded body are not the accommodating section, even when such irregularities are present on a substrate, it is to be noted that such a substrate is defined as a substantially planar substrate.

The "accommodating zone" as referred to herein is an accommodating zone for accommodation as provided in advance on the packaging material for the purpose of accommodating the heat generating composition and is an accommodating zone as described in Japanese Patent No. 3,161,605 and JP-T-11-508314. Since irregularities which are not used for intentionally accommodating the heat generating composition molded body are not the accommodating zone, even when such irregularities are present on a substrate, it is to be noted that such a substrate is defined as a substantially planar substrate.

In the invention, as a heat seal material constituting a heat seal layer, a single raw material may be used, or a composite raw material having a heat seal layer may be used. The heat seal material is not limited so far as at least a part thereof can be welded upon heating. Examples thereof include hot melt based resins such as polyolefins (for example, polyethylene and polypropylene) or olefin copolymer resins, ethylene based hot melt resins (for example, ethylene-vinyl acetate copolymer resins and ethylene-acrylic acid ester copolymer resins (for example, ethylene-isobutyl acrylate copolymer resins)), polyamide based hot melt resins, butyral based hot melt resins, polyester based hot melt resins, polyamide based hot melt resins, polyester based hot melt resins, polymethyl methacrylate based hot melt resins, polyvinyl ether based hot melt resins, polyurethane based hot melt resins, polycarbonate based hot melt resins, such as polyvinyl acetate, and vinyl chloride-vinyl acetate copolymers; and films or sheets thereof. Furthermore, in these hot melt based resins or films or sheets thereof, ones having various additives (for example, an antioxidant) compounded therein can be used. In particular, low density polyethylene and polyethylene obtained by using a metallocene catalyst are useful.

The "bending resistance" as referred to in the invention exhibits rigidity (tension or nerve) or flexibility and follows the A method according to JIS L1096 (45° cantilever method), except for using a heat generating body itself as a sample. That is, a heat generating body is placed on a horizontal table having a smooth surface and having a slope at an angle of 45° in one end thereof such that one side thereof coincides with a scale base line. Next, the heat generating body is slowly slid toward the slope by an appropriate method, and when a central point of the one end of the heat generating body comes into contact with the slope A, the position of the other end is read by a scale. The bending resistance is exhibited by a length (mm) for which the heat generating body moves. Respective five sheets of heat generating body are measured, and the bending resistance (calculated down to the integral place) is expressed by an average value of lengths measured in the length direction and the width direction, or in one direction and the orthogonal direction thereto. However, in the measurement, in the case of measuring an adhesive layer-provided heat generating body such that the adhesive side is faced at the horizontal table side, while the adhesive side provided with a separator is faced at the horizontal table side. In any way, a measured value in the side at which a minimum bending resistance is measured is employed.

Furthermore, in the measurement, the following must be taken into consideration.

(1) A heat generating composition-incorporated exothermic part of the heat generating body is to retain on the horizontal table to an extent of 5 mm or more in width×20 mm or more in length. However, the length is to cross a region where the heat generating composition is present or to cross linearly a region where the heat generating composition is present and a region where the heat generating composition is not present.

(2) In the case of an adhesive layer-provided heat generating body, a plastic film having a bending resistance of not more than 30 mm, or a limp and soft film such as a limp film having a thickness of not more than 50 μm, and preferably not more than 25 μm and a plastic film in which wrinkles are formed by lightly crumpling is to be used as a separator of the adhesive layer and provided along the adhesive layer. Furthermore, with respect to the bending resistance of the substrate and/or the covering material, a specimen of 100 mm×200 mm is prepared, and a bending resistance in the 200 mm direction is employed.

In the invention, the bending resistance in at least one direction is usually not more than 100 mm, preferably not more than 80 mm, more preferably not more than 50 mm, further preferably not more than 30 mm, and still further preferably not more than 20 mm.

A rate of bending resistance of the heat generating body or exothermic part in the invention is a rate of bending resistance to the full length of the heat generating body or exothermic part in one direction and is calculated according to the following expression.

(Rate of bending resistance)=($A/B$)×100

Wherein A represents a bending resistance of the heat generating body or exothermic part in one direction; and B represents the full length of the heat generating body or exothermic part in the foregoing one direction.

In the invention, a rate of bending resistance in at least one direction is usually not more than 50, preferably not more than 40, and more preferably not more than 30.

A ratio of bending resistance in the invention is a ratio of a bending resistance in one direction to a smaller bending resistance in bending resistances in the directions orthogonal thereto in the plane orthogonal to the thickness direction of the heat generating body or exothermic part. The ratio of bending resistance is preferably 2 or more.

In the invention, in the case of a heat generating body having sectional exothermic parts provided at intervals in the striped form, a heat generating body provided with sectional exothermic parts of a parallelepiped shape at intervals in the striped form in which a maximum absolute value of a difference between bending resistances in the two directions as intersecting directions, a heat generating body further provided with an adhesive layer, and a heat generating body provided with adhesive layers at intervals in the striped form are very flexible in one direction and rigid in one direction. Thus, these heat generating bodies relieve symptoms such as stiff shoulders, lower-back pain, and muscular fatigue and especially exhibit efficacy for relieving a symptom of menstrual pain. In addition, these heat generating bodies are able to be wound in a size substantially equal to the width dimension in the width direction of the heat generating body, become compact and are convenient for accommodation.

Furthermore, in the case of a separator-provided heat generating body, by using a separator having a low bending resistance, winding is possible.

Furthermore, in the case of providing a heat generating body along the body, the body includes many two-dimensional curves, and in shoulders, legs, abdomen, waist, arms, and the like, one direction is substantially linear, and the other two directions are formed of a substantially curved surface. Accordingly, since the heat generating body of the invention which is able to form a substantially linear surface in one direction and a curved surface in the other two directions is able to form a two-dimensional curved surface, it is able to well follow the body and is optimum for warming of the body and relaxation or treatment of various symptoms.

Furthermore, in the heat generating body of the invention, by adjusting the size or space of the convex sectional exothermic part, an exothermic part which is flexible and exhibits a uniform temperature distribution or an exothermic part exhibiting a pattern-like temperature distribution is obtainable. By the pattern-like temperature distribution, it is possible to improve a meridian effect of the warming part.

In the heat generating body having sectional exothermic parts, a minimum bending resistance of the bending resistance on the surface orthogonal to the thickness direction is preferably not more than 50 mm, more preferably not more than 40 mm, further preferably not more than 30 mm, and still further preferably from 5 to 30 mm.

The bending resistance and ratio of bending resistance are kept at least at a temperature between 20° C. and 60° C.

The "water retention" as referred to herein is a value as measured and calculated in the following method. That is, about 1 g of a sample fiber as prepared by cutting into a length of about 5 cm and well opening is dipped in pure water, and after elapsing 20 minutes (at 20° C.), water among the fibers is removed using a centrifuge by revolution at 2,000 rpm. A weight (W1) of the thus prepared sample is measured. Next, the sample is dried in a vacuum dryer at 80° C. until it becomes constant in weight, thereby measuring a weight (W2). A water retention is calculated according to the following expression.

[Water retention(%)]=[($W1-W2$)/$W2$]×100

In the invention, the water retention is preferably 20% or more.

In the case of interposing a heat generating composition molded body between a substrate and a covering material, the "temporary adhesion" as referred to in the invention means weak pressure-sensitive bonding or adhesion for the purpose of holding the accommodated heat generating composition molded body until at least the substrate and the covering material are adhered to each other via a sticky layer made of an adhesive and heat sealed.

Furthermore, the "deadhesion" as referred to herein means that in the temporary adhering seal part after heat seal, the heat generating composition in a non-heat sealed region is transferred to the foregoing region, thereby releasing the temporary adhesion.

The temporary adhering seal part is formed via a sticky layer. An adhesive constituting the sticky layer is not limited so far as it is a layer formed of a polymer composition which is tacky at the normal temperature and can be heat sealed after the temporary adhesion.

Furthermore, although the adhesive of the foregoing adhesive layer can be used as the adhesive constituting the sticky layer to be used for the temporary adhesion, a non-hydrophilic adhesive is preferable. As the adhesive constituting the sticky layer, one which is well compatible with the heat seal material constituting the heat seal is preferable, and a melting point of a base polymer of the adhesive is preferably not higher than a melting point of the heat seal material. In particular, hot melt based adhesives are preferable. Furthermore, in the case where the heat seal material is made of an olefin based raw material, preferred examples of the adhesive include olefin based adhesives.

Incidentally, a method for providing a sticky layer for the temporary adhesion is not limited. The sticky layer may be entirely provided or partially or intermittently provided. Examples of its shape include various shapes such as a network-like shape, a stripe-like shape, a dot-like shape, and strip-like shape.

The heat generating body of the invention is able to give various shapes, thicknesses and temperature zones and therefore, can be used for various utilities such as use for a joint, facial esthetic use, use for eyes, slimming use, use for heating or warming a dripping solution, use for a wet compress pack, use for a medical body warmer, use for a neck, use for a waist, use for a mask, use for a glove, use for hemorrhage, use for relaxation of symptoms such as shoulder pain, muscular pain, and menstrual pain, use for a cushion, use for heating or warming a human body during the operation, use for a thermal sheet, use for thermally volatilizing an aroma, use for an abdomen, insecticidal use by thermal volatilization, and use for treating cancer in addition to common warming of a human body. In addition, the heat generating body of the invention can be used for heating or warming machines, pets, etc.

For example, in the case of using for relaxation of symptoms, the heat generating body of the invention is applied directly in a necessary site of the body or indirectly via a cloth, etc. Furthermore, in the case of using for heating or warming a human body during the operation, a method for using the heat generating body of the invention includes the following methods.

(1) The heat generating body is directly applied to a body requiring heating or warming.

(2) The heat generating body is fixed on a covering, etc. and covered on the body.

(3) The heat generating body is fixed on a cushion to be placed beneath the body, etc.

(4) The heat generating body is used as a covering or a cushion which is a product having the heat generating body provided therein in advance.

Incidentally, examples of the pain of muscles or bones include acute muscle pain, acute bone pain, acute reference pain, previous muscle pain, previous bone pain, chronic reference pain, and join pain of knee, elbow, etc.

The holding time is not limited but is preferably from 20 seconds to 24 hours, more preferably from one hour to 24 hours, and further preferably from 8 hours to 24 hours.

The holding temperature is preferably from 30 to 50° C., more preferably from 32 to 50° C., further preferably from 32 to 43° C., still further preferably from 32 to 41° C., and even further preferably from 32 to 39° C.

Preferred embodiments of the heat generating body of the invention will be described below with reference to the accompany drawings.

BRIEF DESCRIPTION OF THE DRAWINGS

FIG. 4 is a cross-sectional view of other embodiment of the heat generating body of the invention.

FIG. 5 is a plan view of other embodiment of the heat generating body of the invention.

FIG. 6 is a plan view of other embodiment of the heat generating body of the invention.

FIG. 7 is a plan view to show modifications of the shape of the heat generating body of the invention.

DESCRIPTION OF REFERENCE NUMERALS AND SIGNS

| | |
|---|---|
| 1: | Heat generating body |
| 2: | Heat generating composition molded body |
| 3: | Sectional exothermic part |
| 4: | Sectioned part |
| 5: | Circumferential seal part |
| 6: | Substrate |
| 7: | Covering material |
| 8: | Adhesive layer |
| 8A: | Air-permeable adhesive layer |
| 9: | Separator |
| 10: | Pushing plate |
| 11: | Flat plate |
| 12: | Non-water absorptive film (for example, a polyethylene film) |
| 13: | Filter paper in which eight lines are drawn radiating from the center point with an interval of 45° |
| 14: | Die plate having a hollow cylindrical hole |
| 15: | Hole |
| 16: | Sample |
| 17: | Stainless steel plate |
| 18: | Distance to the oozed-out locus of water or aqueous solution |
| 19: | Position corresponding to a hollow cylindrical hole on filter paper |

Examples

Figure 1:
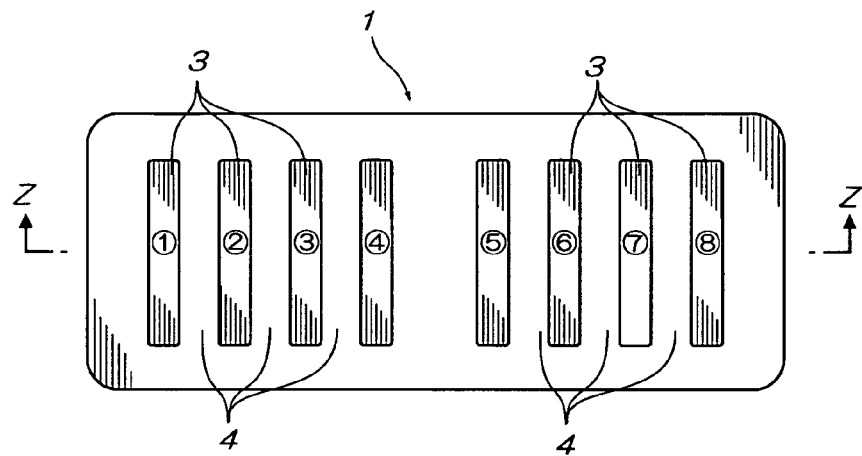
FIG. 1 is a plan view of an embodiment of the heat generating body of the invention.
Figure 2:
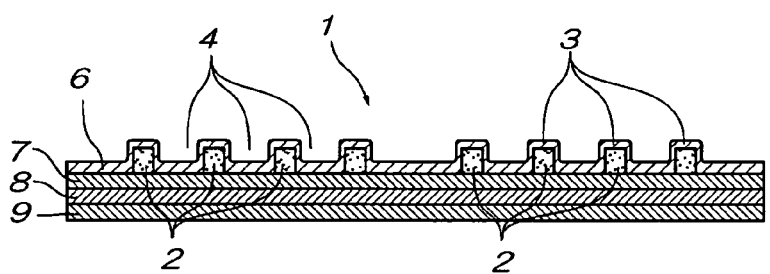
FIG. 2 is a cross-sectional view along the line Z-Z of the same.

A heat generating body 1 of an embodiment as shown in FIG. 1 and FIG. 2 has an irregular sheet-like shape, is composed of eight sectional exothermic parts 3 each having a heat generating composition molded body and is provided with low temperature sectional exothermic parts 1 and 8 which generate a maximum temperature of low temperature, middle temperature sectional exothermic parts 2, 3, 6 and 7 which generate a maximum temperature of middle temperature, and high temperature sectional exothermic parts 4 and 5 which generate a maximum temperature of high temperature.

In the invention, as a method for making the maximum temperature as generated by the high temperature exothermic part of the heat generating body higher than the maximum temperature as generated by the low temperature exothermic part and making the maximum temperature as generated by the middle sectional exothermic part laid therebetween, there is (1) a method while taking into consideration a heat insulating effect due to the disposition of the sectional exothermic parts.

With respect to the respective sectional exothermic parts, examples of other methods include (2) a method in which the planar area of each of the sectional exothermic parts is made different; (3) a method in which the amount of air of the air-permeable sheet covering the heat generating body is made different; and (4) a method in which the kind, the composition or the compression rate of the heat generating body is made different.

These methods may be employed singly or may be properly combined. Furthermore, the distance between the sectional exothermic parts may be either a fixed distance or a non-fixed distance.

In any way, desired temperature distribution is not obtained unless a heat insulating effect from the surroundings is taken into consideration.

The foregoing method (1) utilizes the matter that the higher the heat insulating effect, the higher the maximum temperature. This method has such an advantage that the maximum temperature of each of the sectional exothermic parts can be made different by making the respective sectional exothermic parts identical with each other with respect to the amount of air, the planar area and the height of each of the sectional exothermic parts and making the heat generating composition molded bodies identical with each other with respect to the basis weight.

For example, the heat generating body as shown in FIG. 1 and FIG. 2 has eight sectional exothermic parts; the respective sectional exothermic parts have substantially the same amount of air (about 400 g/mm$^2$/24 hr); and the sectional exothermic parts have a shape of 100 mm in length×5 mm in width×3.5 mm in height and provided at intervals of 5 mm.

A heat generating composition having a water mobility value of 4.3, which is a mixture consisting of 100 parts by weight of a reduced iron powder (particle size: not more than 300 μm), 7.0 parts by weight of active carbon (particle size: not more than 300 μm), 5.0 parts by weight of a wood meal (particle size: not more than 300 μm), 0.8 parts by weight of a water absorptive polymer (particle size: not more than 300 μm), 0.2 parts by weight of calcium hydroxide, 0.7 parts by weight of sodium sulfite and 11% of salt water, was used.

A substrate is made of a polyethylene film 7 which is provided with a 30 μm-thick acrylic adhesive layer 8 provided with a separator 9.

A covering material 6 was a laminate of a 70 μm-thick polyethylene-made porous film and a nylon-made non-woven fabric with a basis weight of 40 g/m$^2$ and had an air permeability of 400 g/m$^2$/24 hr in terms of a moisture permeability by the Lyssy method. The heat generating composition was molded into a heat generating composition molded body of a parallelepiped by die molding.

The respective sectional exothermic parts 3 were made identical with each other with respect to the amount of air, the planar area and the height, and the heat generating composition molded bodies were made identical with each other with respect to the basis weight. That is, the respective heat generating composition molded bodies 2 have a size of 100 mm in length×10 mm in width×3.5 m min height. A distance between the sectional exothermic parts was set up at 5 mm. However, a space in the central part was set up at 10 mm.

Accordingly, a center point distance between 1 and 2, between 2 and 3, between 3 and 4, between 5 and 6, between 6 and 7 and between 7 and 8 is 10 mm, respectively; and a center point distance between 4 and 5 is 20 mm.

Since other matters than the distance are all identical, the temperature factor is calculated by a center distance method as follows.

$$T1 = \frac{1}{10} + \frac{1}{20} + \frac{1}{30} + \frac{1}{50} + \frac{1}{60} + \frac{1}{70} + \frac{1}{80} = 0.243 \quad \text{Re: 1}$$

$$T2 = \frac{1}{10} + \frac{1}{10} + \frac{1}{20} + \frac{1}{40} + \frac{1}{50} + \frac{1}{60} + \frac{1}{70} = 0.325 \quad \text{Re: 2}$$

$$T3 = \frac{1}{10} + \frac{1}{20} + \frac{1}{10} + \frac{1}{30} + \frac{1}{40} + \frac{1}{50} + \frac{1}{60} = 0.341 \quad \text{Re: 3}$$

$$T4 = \frac{1}{10} + \frac{1}{20} + \frac{1}{30} + \frac{1}{20} + \frac{1}{30} + \frac{1}{40} + \frac{1}{50} = 0.341 \quad \text{Re: 4:}$$

5 is the same as 4; 6 is the same as 3; 7 is the same as 2; and 8 is the same as 1.

Figure 3:
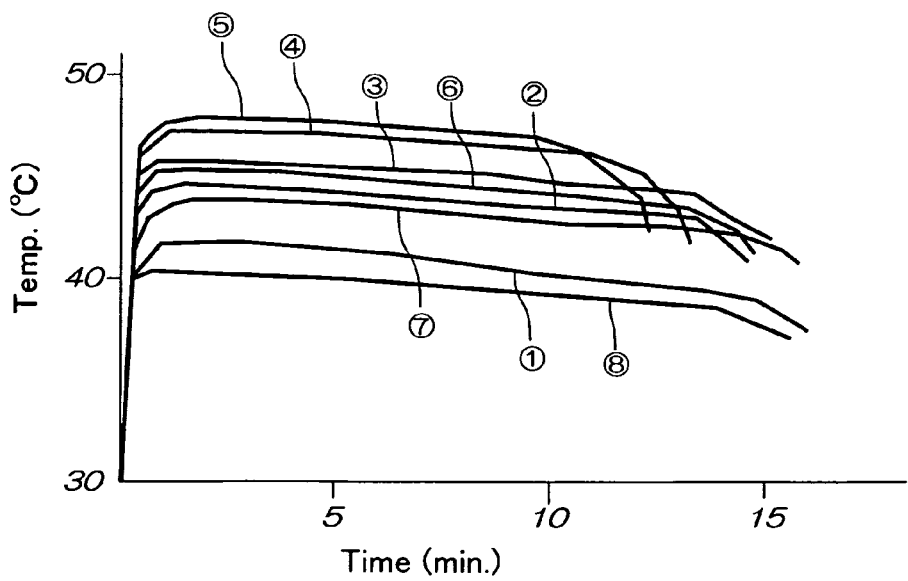
FIG. 3 is a diagram of exothermic characteristics of the heat generating body of the invention.
Figure 8:
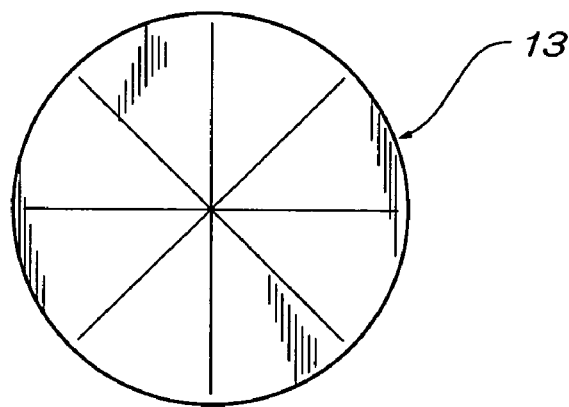
FIG. 8 is a plan view of a filter paper for the measurement of water mobility value in the invention.
Figure 9:
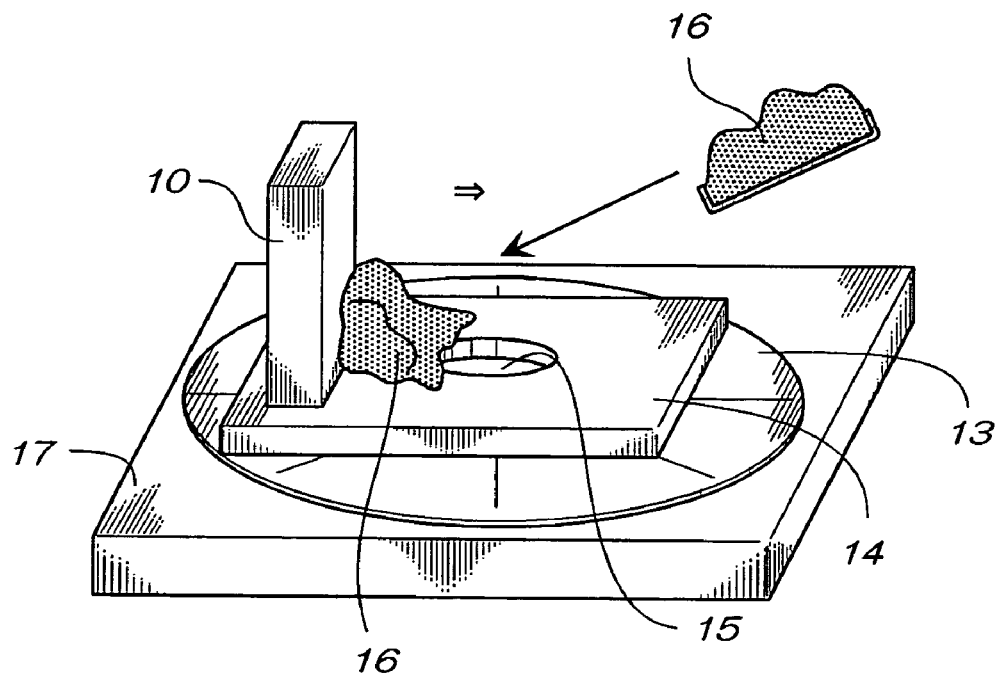
FIG. 9 is an oblique view for explaining the measurement of water mobility value in the invention.
Figure 10:
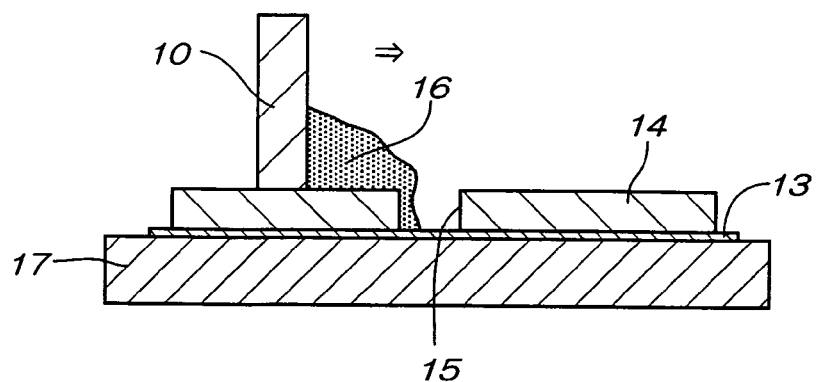
FIG. 10 is a cross-sectional view for explaining the measurement of water mobility value in the invention.
Figure 11:
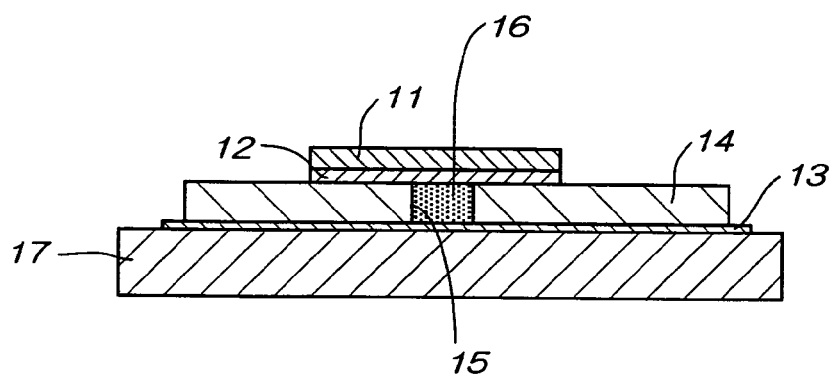
FIG. 11 is a cross-sectional view for explaining the measurement of water mobility value in the invention.
Figure 12:
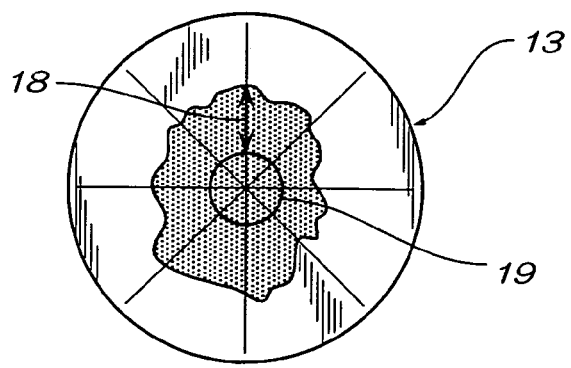
FIG. 12 is a plan view of a filter paper after carrying out the measurement of water mobility value in the invention.

Accordingly, the high temperature exothermic part is corresponding to 3, 4, 5 and 6; the middle temperature exothermic part is corresponding to 2 and 7; and the low temperature exothermic part is corresponding to 1 and 8. On the basis of this, the heat generating body 1 was produced and then subjected to an exothermic test, thereby obtaining exothermic characteristics as shown in FIG. 3. 3, 4, 5 and 6 each exhibited almost 47° C. and constituted a high temperature exothermic part; 2 and 7 each exhibited almost 45° C. and constituted a middle temperature sectional exothermic part; and 1 and 8 each exhibited almost 40° C. and constituted a low temperature exothermic part, respectively.

Furthermore, a heat generating body of other embodiment as shown in FIG. 6 is in an irregular sheet-like shape, has a broad bean-like shape and is composed of ten sectional exothermic parts 3 each having a planar elliptical shape and having an elliptical heat generating composition molded body. This heat generating body was produced by using the same heat generating composition, substrate and covering material as in Example 1. The heat generating composition was compressed within a die by using a trimming die having ten cavities each having a planar elliptical shape and having a die thickness of 4 mm to mold a heat generating composition molded body having a thickness of 3.5 mm, which was then contained in the sectional exothermic part.

The respective sectional exothermic parts 3 were made identical with each other with respect to the amount of air, the planar area and the height, and the heat generating composition molded bodies were made identical with each other with respect to the composition, the compression rate and the basis weight.

Furthermore, 1, 2, 3, 7 and 8 were disposed symmetrically with 4, 5, 6, 9 and 10 in the central part.

Accordingly, 1 and 6, 2 and 5, 3 and 4, 7 and 10, and 8 and 9 are made laid under the same condition, respectively.

The center point distance between the respective sectional exothermic parts was designed as shown in Table 1.

TABLE 1

|   | 1 | 2 | 3 | 4 | 5 | 6 | 7 | 8 | 9 | 10 |
|---|---|---|---|---|---|---|---|---|---|----|
| 1 | — | 40 mm | 75 mm | 115 mm | 145 mm | 180 mm | 40 mm | 73 mm | 115 mm | 146 mm |
| 2 | — | — | 35 mm | 78 mm | 110 mm | 145 mm | 40 mm | 50 mm | 85 mm | 115 mm |
| 3 | — | — | — | 45 mm | 77 mm | 116 mm | 57 mm | 45 mm | 60 mm | 90 mm |
| 4 | — | — | — | — | 35 mm | 75 mm | 90 mm | 63 mm | 45 mm | 57 mm |
| 5 | — | — | — | — | — | 40 mm | 115 mm | 84 mm | 50 mm | 40 mm |

TABLE 1-continued

| 1 | 2 | 3 | 4 | 5 | 6 | 7 | 8 | 9 | 10 |
|---|---|---|---|---|---|---|---|---|---|
| 6 | — | — | — | — | — | — | 145 mm | 112 mm | 73 mm | 40 mm |
| 7 | — | — | — | — | — | — | — | 35 mm | 75 mm | 110 mm |
| 8 | — | — | — | — | — | — | — | — | 45 mm | 45 mm |
| 9 | — | — | — | — | — | — | — | — | — | 35 mm |
| 10 | — | — | — | — | — | — | — | — | — | — |

From the foregoing, the temperature factors of the respective center points are as follows.

$$T1=T6=0.1137$$

$$T2=T5=0.1479$$

$$T8=T9=0.1544$$

$$T7=T10=0.1547$$

$$T3=T4=0.1621$$

With respect to the temperature distribution by the exothermic test of the heat generating body 1, 3 and 4 exhibited almost 47° C. and formed a high temperature exothermic part; 1 and 6 exhibited almost 40° C. and formed a low temperature exothermic part; and 2, 5, 8, 9, 7 and 10 exhibited almost from 43 to 45° C. and formed a middle temperature exothermic part, respectively.

The heat generating body of this Example is provided with the low temperature sectional heat generating parts 1 and 6 which generate a maximum temperature of low temperature; the middle temperature sectional exothermic parts 2, 5, 6, 7, 8 and 9 which generate a maximum temperature of middle temperature; and the high temperature sectional exothermic parts 3 and 4 which generate a maximum temperature of high temperature.

Incidentally, the composition and the basis weight of the heat generating body are identical among the low temperature sectional exothermic part, the middle temperature sectional exothermic part and the high temperature sectional exothermic part in the heat generating body. For that reason, the heat generating body is low in production costs, excellent in storage, transportation and handling properties during the use and excellent in appearance.

Furthermore, the heat generating body was sealed and accommodated in an air-impermeable accommodating bag (hereinafter referred to as "outer bag") and allowed to stand at room temperature for 24 hours. After 24 hours, the heat generating body was taken out from the outer bag and then subjected to an exothermic test for the body. As a result, it was felt warm within 3 minutes, and the warmth was continued for 7 hours. At the same time, curved surface fitness, winding properties and usefulness were evaluated. As a result, the heat generating body was superior in all of these evaluations.

FIG. 4 is a cross-sectional view of other embodiment of a heat generating body 1 having an air-permeable adhesive layer 8A on the air-permeable surface of the heat generating body 1 by a melt blow method.

A batchwise stirring tank composed of a mixer equipped with a rotary blade in a blade form of a ventilation fan was used as an oxidizing gas contact treatment device, and air was used as an oxidizing gas.

First of all, a reaction mixture consisting of 100 parts by weight of a reduced iron powder (particle size: not more than 300 μm), 3.5 parts by weight of active carbon (particle size: not more than 300 μm) and 5 parts by weight of 11% salt water and having a water mobility value of less than 0.01 was charged in the contact treatment device vessel.

Next, the upper portion of the contact treatment device vessel was opened to air, and the reaction mixture was subjected to self heat generation with stirring in the opened state to air under circumstances at 20° C. When the maximum exothermic temperature reached 25° C., 5 parts by weight of a wood meal (particle size: not more than 300 μm), 1.2 parts by weight of a water absorptive polymer (particle size: not more than 300 μm), 0.2 parts by weight of calcium hydroxide, 0.7 parts by weight of sodium sulfite and 11% salt were mixed therewith to obtain a heat generating composition having a water mobility value of 10.

Next, by using the trimming die as used in Example 1, a heat generating composition molded body 2 was molded, and a laminate of a napped non-woven fabric and a polyethylene film was laminated on a substrate 7 provided with a heat seal layer made of polyethylene and 5% by weight EVA in the polyethylene side. Next, a covering material 6 the same as in Example 1 was put thereon; the surroundings of the heat generating composition molded body 2 were heat sealed; an SES based hot melt based adhesive layer 8A in a cobweb form was provided in the side of the air-permeable covering material 6 by a melt blow method; and a separator 9 was then provided thereon, followed by cutting to obtain a heat generating body 1. This heat generating body 1 was sealed and accommodated in an outer bag and allowed to stand at room temperature for 24 hours. After 24 hours, the heat generating body 1 was taken out from the outer bag and after removing the separator, subjected to an exothermic test for the body. As a result, it was felt warm within 3 minutes, and the warmth was continued for 7 hours. At the same time, curved surface fitness, winding properties and usefulness were evaluated. As a result, the heat generating body was superior in all of these evaluations.

Since the heat generating body 1 is provided with low temperature sectional exothermic parts 1 and 8, middle temperature sectional exothermic parts 2, 3, 6 and 7, and high temperature sectional exothermic parts 4 and 5, each having a different maximum temperature, even when put over a long period of time, it is possible to efficiently warm a site as intended to be warmed while hardly imparting an unwell feeling due to the high temperature to a user. That is, not only a portion to be especially warmed (for example, an acupuncture point and a center point) can be warmed with concentration by the high temperature sectional exothermic part, but also the surroundings thereof can be mildly warmed by the middle sectional exothermic part and the low temperature sectional exothermic part. In this way, an unwell feeling due to the high temperature of the high temperature sectional exothermic part can be suppressed while obtaining an excellent warming effect (for example, an effect for relaxation of pains due to a thermal stimulus) due to the high temperature of the high temperature sectional exothermic part. Since this heat generating body gives rise to such effects, it can be suitably used for relaxation of menstrual pain, relaxation of low-back pain, relaxation of stiff shoulder, and so on. Furthermore, in the heat generating body, since the low temperature sectional exothermic part, the middle temperature sectional exothermic part and the high temperature sectional exothermic part are continuously provided by connecting parts not having a heat generating body, the heat generating body can be easily bent in the connecting parts and even by long-term use, is hardly peeled off inadvertently so that a stable wearing feeling is obtained.

Furthermore, in the heat generating body 1, the composition and the basis weight of the heat generating composition molded body are identical among the low temperature sectional exothermic part, the middle temperature sectional exothermic part and the high temperature sectional exothermic part, and the maximum temperature as generated in each of the low temperature sectional exothermic part, the middle temperature sectional exothermic part and the high temperature sectional exothermic part is made different by the foregoing method (1). Thus, not only its production is extremely easy, but also its appearance, storage, transportation and handling properties during the use are excellent.

In addition, with respect to the heat generating body, since one having a structure in which a high temperature sectional exothermic part is provided in the central part thereof has a high temperature sectional exothermic part in the central part thereof, an unwell feeling due to the high temperature by the high temperature sectional exothermic part is especially effectively suppressed by a middle temperature sectional exothermic part or a low temperature sectional exothermic part. Furthermore, as other embodiment, one in which a low temperature sectional exothermic part, a middle temperature sectional exothermic part and a high temperature sectional exothermic part are properly disposed, various thermal stimuli can be taken so that a warming effect can be much more enhanced.

FIG. 5 is a plan view of other embodiment of a heat generating body 1 having a constitution in which sectional exothermic parts 3 are provided in a striped form; an end part thereof is a low temperature sectional exothermic part; a central part thereof is a high temperature sectional exothermic part; and a middle part between the central part and the end part is a middle temperature sectional exothermic part.

FIG. 7 shows modifications of the shape of the heat generating body. (a) shows a broad bean-like shape; (b) shows an eye mask-like shape; (c) shows a cocoon-like-shape; (d) shows a gourd-like shape; (e) shows a rectangular shape with rounded corners; (f) shows a rectangular shape; (g) shows a square shape with rounded corners; (h) shows a square shape; (i) shows an egg-like shape; (j) shows a boomerang-like shape; (k) shows a comma-shaped bead-like shape; (l) shows a wing-like shape; (m) shows a wing-like shape; (n) shows a star-like shape; (o) shows a nose-like shape; (p) shows a paper lantern-like shape; and (q) shows a paper lantern-like shape, respectively.

The invention claimed is:

1. A heat generating body wherein three or more plural sectional exothermic parts are provided at intervals via a sectioned part which is a heat seal part, characterized in that:
    the sectional exothermic parts have a heat generating composition capable of causing heat generation upon contact with oxygen in air and are at least constituted of three kinds of a low temperature sectional exothermic part, a middle temperature sectional exothermic part and a high temperature sectional exothermic part;
    a maximum temperature of the high temperature sectional exothermic part is higher than a maximum temperature of the low temperature sectional exothermic part;
    a maximum temperature of the middle temperature sectional exothermic part is laid between a maximum temperature of the high temperature sectional exothermic part and a maximum temperature of the low temperature sectional exothermic part; and
    the middle temperature sectional exothermic part is constituted of plural sectional exothermic parts having a different maximum temperature.

2. The heat generating body according to claim 1, characterized in that:
    the heat generating composition is a moldable heat generating composition which contains, as essential components, an iron powder, a carbon component, a reaction accelerator and water, does not contain a flocculant aid, a flocculant, an agglomeration aid, a dry binder, a dry binding agent, a dry binding material, a sticky raw material, a thickener and an excipient, contains surplus water so as to have a water mobility value of from 0.01 to 20, has moldability due to the surplus water which is a connecting substance, with the water in the heat generating composition not functioning as a barrier layer, and is capable of causing an exothermic reaction upon contact with air;
    a heat generating composition molded body as formed by molding the moldable heat generating composition is laminated on a substrate, a covering material is put thereon, and the periphery of the heat generating composition molded body is heat sealed to form the sectional exothermic parts;
    the substrate is substantially planar and does not have a pocket, an accommodating division or an accommodating zone;
    the heat generating composition molded body has a volume of from 0.1 to 30 cm$^3$;
    a ratio of the capacity of the sectional exothermic parts to the volume of the heat generating composition molded body is from 0.6 to 1.0;
    the sectioned exothermic parts have a maximum height of from 0.1 to 10 mm;
    the sectioned part between the sectional exothermic parts has a width of from 0.3 to 50 mm; and
    the substrate or the covering material has permeability to air.

3. The heat generating body according to claim 1, characterized in that the low temperature sectional exothermic part, the middle temperature sectional exothermic part and the high temperature sectional exothermic part are determined by a center distance method.

4. The heat generating body as set forth in claim 1, characterized in that the heat generating body has the low temperature sectional exothermic part in end part thereof.

5. The heat generating body according to claim 1, characterized in that on the surface orthogonal to the thickness of the heat generating body, a bending resistance in at least one direction is not more than 100 mm.

6. The heat generating body according to claim 1, characterized in that the heat generating body has a fixing measure.

* * * * *